US009745341B2

(12) United States Patent
Vlahov et al.

(10) Patent No.: US 9,745,341 B2
(45) Date of Patent: *Aug. 29, 2017

(54) TUBULYSINS AND PROCESSES FOR PREPARING

(71) Applicant: ENDOCYTE, INC., West Lafayette, IN (US)

(72) Inventors: Iontcho Radoslavov Vlahov, West Lafayette, IN (US); Christopher Paul Leamon, West Lafayette, IN (US); Kevin Yu Wang, Zionsville, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,196

(22) Filed: Oct. 23, 2015

(65) Prior Publication Data
US 2016/0108085 A1 Apr. 21, 2016

Related U.S. Application Data

(63) Continuation of application No. 12/739,579, filed as application No. PCT/US2008/080948 on Oct. 23, 2008, now Pat. No. 9,187,521.

(60) Provisional application No. 61/036,176, filed on Mar. 13, 2008, provisional application No. 60/982,595, filed on Oct. 25, 2007.

(51) Int. Cl.
*A61K 31/445* (2006.01)
*C07K 5/02* (2006.01)
*C07K 5/078* (2006.01)

(52) U.S. Cl.
CPC .......... *C07K 5/021* (2013.01); *C07K 5/06139* (2013.01)

(58) Field of Classification Search
None
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 4,166,810 A | 9/1979 | Cullinan et al. |
| 4,203,898 A | 5/1980 | Cullinan et al. |
| 4,337,339 A | 6/1982 | Farina et al. |
| 4,691,024 A | 9/1987 | Sirahata |
| 4,713,249 A | 12/1987 | Schroder |
| 4,801,688 A | 1/1989 | Laguzza et al. |
| 4,866,180 A | 9/1989 | Vyas et al. |
| 5,006,652 A | 4/1991 | Cullinan et al. |
| 5,094,849 A | 3/1992 | Cullinan et al. |
| 5,108,921 A | 4/1992 | Low et al. |
| 5,140,104 A | 8/1992 | Coughlin et al. |
| 5,266,333 A | 11/1993 | Cady |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,291,673 B1 | 9/2001 | Fuchs et al. |
| 6,291,684 B1 | 9/2001 | Borzilleri et al. |
| 6,335,434 B1 | 1/2002 | Guzaev et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Molnar-Kimber et al. |
| 6,596,757 B1 | 7/2003 | Chari et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Steinmetz et al (Angew Chem Int Ed 43:4888-4892, 2004).*
Lopes et al (J Chem Soc (Perkin Trans 2) 3:431-440, 1999).*
Speckamp et al (Tetrahedron 56:3817-3856, 2000).*
Agoston E.S. et al., "Vitamin D Analogs as Anti-Carcinogenic Agents," *Anti-Cancer Agents in Medicinal Chemistry,* 2006; 6(1): 53-71.
Anderson et al., "Potocytosis: Sequestration and transport of small molecules by caveolae," *Science,* 1992; 255: 410-411.
Antony A.C., "Folate receptors," *Annu Rev Nutr,* 1996; 16: 501-21.
Antony A.C., "The biological chemistry of folate receptors," *Blood,* 1992; 79(11):2807-2820.

(Continued)

*Primary Examiner* — Craig Ricci
(74) *Attorney, Agent, or Firm* — Barnes & Thornburg LLP

(57) ABSTRACT

Processes are described for the preparation of tubulysins. The processes are useful for preparing predetermined mixtures of tubulysins, preparing single tubulysins from mixtures of tubulysins, and for converting one tubulysin into a different tubulysin. The tubulysins described herein are useful in treating diseases and disease states that include pathogenic cell populations.

20 Claims, No Drawings

(56) References Cited

U.S. PATENT DOCUMENTS

| | | |
|---|---|---|
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Kim et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,601,332 B2 | 10/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Domling et al. |
| 7,875,612 B2 | 1/2011 | Green et al. |
| 8,044,200 B2 | 10/2011 | Xu et al. |
| 8,105,568 B2 | 1/2012 | Vlahov et al. |
| 8,288,557 B2 | 10/2012 | Vlahov et al. |
| 8,465,724 B2 | 6/2013 | Vlahov et al. |
| 8,470,822 B2 | 6/2013 | Green et al. |
| 8,765,096 B2 | 7/2014 | Leamon et al. |
| 8,889,880 B2 | 11/2014 | Vlahov et al. |
| 9,090,563 B2 | 7/2015 | Vlahov et al. |
| 9,138,484 B2 | 9/2015 | Leamon et al. |
| 9,187,521 B2 | 11/2015 | Vlahov et al. |
| 2003/0086900 A1 | 5/2003 | Low et al. |
| 2003/0162234 A1 | 8/2003 | Jallad |
| 2004/0018203 A1 | 1/2004 | Pastan et al. |
| 2004/0033195 A1 | 2/2004 | Leamon et al. |
| 2004/0242582 A1 | 12/2004 | Green et al. |
| 2005/0004010 A1 | 1/2005 | Collins et al. |
| 2005/0026068 A1 | 2/2005 | Gogolides et al. |
| 2005/0107325 A1 | 5/2005 | Mancharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2006/0058266 A1 | 3/2006 | Manoharan et al. |
| 2006/0128754 A1* | 6/2006 | Hoefle ............... C07D 417/12 514/326 |
| 2007/0009434 A1 | 1/2007 | Low et al. |
| 2007/0275904 A1 | 11/2007 | Vite et al. |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2010/0004276 A1 | 1/2010 | Vlahov et al. |
| 2010/0048490 A1 | 2/2010 | Vlahov et al. |
| 2010/0104626 A1 | 4/2010 | Leamon et al. |

FOREIGN PATENT DOCUMENTS

| | | |
|---|---|---|
| EP | 0116208 | 3/1988 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO 88/01622 | 3/1988 |
| WO | WO 90/12096 | 10/1990 |
| WO | WO 91/07418 | 5/1991 |
| WO | WO96/36367 | 11/1996 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO 01/28592 | 4/2001 |
| WO | WO 01/74382 | 10/2001 |
| WO | WO 02/085908 | 10/2002 |
| WO | WO 02/087424 | 11/2002 |
| WO | WO 02/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO 2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO 2005/112919 | 12/2005 |
| WO | WO 2006/012527 | 2/2006 |
| WO | WO 2006/042146 | 4/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |
| WO | 2011/069116 | 6/2011 |
| WO | 2011/106639 | 11/2011 |
| WO | 2012/019123 | 2/2012 |

OTHER PUBLICATIONS

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.

Archer M.C. et al., "Separation of Folic Acid Derivatives and Pterins by High-Performance Liquid Chromatography," *Methods in Enzymology*, 1980; 66: pp. 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Birinberg E. M. et al., "Synthesis and antimetabolic activity of pyrimidine analogs of folic and pteroic acids," *Pharmaceutical Chemistry Journal*, 1969; 3(6): pp. 331-333.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem.* 8(3): 338-346 (1997).

Christensen et al., "Membrane receptors for endocytosis in the renal proximal tubule," *Int. Rev. Cytol.*, 1998; 180: 237-284.

(56) References Cited

OTHER PUBLICATIONS

Citro G. et al., "Inhibition of leukemia cell proliferation by folic acid—polylysine-mediated introduction of c-*myb* antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
DeVita, Jr., Vincent et al (eds); *Biologic Therapy of Cancer*; 2nd ed., J.B. Lippincott Company; 1995.
Domling A. et al., "Myxobacterial Epothilones and Tubulysins as Promising Anticancer Agents," *Molecular Diversity*, 2005; 9: 141-147.
Douglas J.T. et al., "Targeted Gene Delivery by Tropism-Modified Adenoviral Vectors," *Nat. Biotechnol.*, 1996, vol. 14, pp. 1574-1578.
Eichman, J.D. et al., "The Use of PAMAM Dendrimers in the Efficient Transfer of Genetic Material Into Cells", Jul. 2000, *PSTT*, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
Greene T.E. et al., "Protective Groups in Organic Synthesis," 2d edition, John Wiley & Sons, Inc. New York (1991).
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.
Hofland et al., "Folate-targeted gene transfer in vivo," *Mol Ther* 5(6): 739-744 (2002).
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Holladay et al., "Riboflavin-mediated delivery of a macromolecule into cultured human cells," *Biochim Biophys Acta*, 1426(1): 195-204 (1999).
U.S. Appl. No. 60/946,092, filed Jun. 25, 2007, Vlahov et al.
U.S. Appl. No. 60/982,595, filed Oct. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.
Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
U.S. Appl. No. 12/775,824, filed May 7, 2010, Green et al.
U.S. Appl. No. 12/666,712, filed Dec. 24, 2009, Leamon et al.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kim et al., "Synthesis and biological activity of 10-thia-10-deaza analogs of folic acid, pteroic acid, and related compounds", *Journal of Medical Chemistry*, 18: 776-780 (1975).
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in Lactobacillus salivarius. Characterization of the transport mechanism and purification and properties of the binding component," *J. Biol. Chem..* 1987; 262(15):7171-7179.
Ladino et al., "Folate-maytansinoids: target-selective drugs of low molecular weight," *Int. J. Cancer*, 73(6): 859 864 (1997).
Lambooy J. P., "Riboflavin Analogs Utilized for Metabolism by a Lactobacillus Casei Mutant," *Int. J. Biochem.*, vol. 16, No. 2, 1984, pp. 231-234.
Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Larock R.C., "Comprehensive Organic Transformations, a guide to functional group preparations," VCH Publishers, Inc. New York (1989).

(56) References Cited

OTHER PUBLICATIONS

Leamon CP et al, "Cytotoxicity of folate-Pseudomonas exotoxin conjugates toward tumor cells. Contribution of translocation domain," J. Biol. Chem. 268(33): 24847-24854 (1993).
Leamon CP et al., "Comparative Preclinical Activity of the Folate-targeted Vinca Alkaloid Conjugates EC140 and EC145," Int J Cancer, 2007; 121(7):1585-92.
Leamon CP et al., "Cytotoxicity of momordin-folate conjugates in cultured human cells," J. Biol. Chem., 1992; 267(35): 24966-24971.
Leamon CP et al., "Delivery of macromolecules into living cells: a method that exploits folate receptor endocytosis," Proc. Natl. Acad. Sci. USA 88(13): 5572-5573 (1991).
Leamon CP et al., "Folate-mediated targeting: from diagnostics to drug and gene delivery," Drug Discovery Today 6: 36-43 (2001).
Leamon CP et al., "Folate-targeted chemotherapy," Adv Drug Deliv Rev, 2004;56(8): 1127-41.
Leamon CP et al., "Membrane folate-binding proteins are responsible for folate-protein conjugate endocytosis into cultured cells," Biochem. J. 291: 855-860 (1993).
Leamon CP et al., "Selective targeting of malignant cells with cytotoxin-folate conjugates," J. Drug Target. 2(2): 101-112 (1994).
Leamon CP et al., "Synthesis and biological evaluation of EC140: A novel folate-targeted vinca alkaloid conjugate," Bioconjug Chem, 2006;17(5):1226-32.
U.S. Appl. No. 60/590,580, filed Jul. 23, 2004, Vlahov et al.
Leamon CP et al., "Synthesis and Biological Evaluation of EC20: A New Folate-Derived, (99m)Tc-Based Radiopharmaceutical," Bioconjug. Chem. 13(6): 1200-1210 (2002).
Leamon CP et al., "Synthesis and biological evaluation of EC72: a new folate-targeted chemotherapeutic," Bioconjug Chem., 2005;16(4):803-11.
Leamon et al., "Folate-mediated drug delivery: effect of alternative conjugation chemistry," J. Drug Target 7(3): 157-169 (1999).
Lee et al, "Measurement of Endosome pH Following Folate Receptor-Mediated Endocytosis," Biochim. Biophys. Acta 1312(3): 237-242 (1996).
Lee W.W. et al., "Folic acid antagonists. Methotrexate analogs containing spurious amino acids. Dichlorohomofolic acid," Journal of Medical Chemistry, 17: 326-330 (1974).
Lee et al., "Synthesis and evaluation of taxol-folic acid conjugates as targeted antineoplastics," Bioorg Med Chem. 10(7): 2397-2414, (2002).
Lee, R. J. and Huang, L., "Folate-Targeted, Anionic Liposome-Entrapped Polylysine-Condensed Dna for Tumor Cell-Specific Gene Transfer," J. Biol. Chem. 271(14): 8481-8487 (1996).
Lee, R. J. and Low, P. S, "Delivery of liposomes into cultured KB cells via folate receptor-mediated endocytosis," J. Biol. Chem. 269(5): 3198-3204 (1994).
Lee, R. J. and Low, P. S., "Folate-mediated tumor cell targeting of liposome-entrapped doxorubicin in vitro," Biochim. Biophys. Acta 1233: 134-144 (1995).
Lemon, Julia, et al., "Conversion of Pterolyglutamic Acid to Pteroic Acid by Bacterial Degradation," Archives of Biochemistry, 1948; vol. 19, pp. 311-316.
Levy, Carl C., et al. "The Enzymatic Hydrolysis of Methotrexate and Folic Acid", 1967, The Journal of Biological Chemistry, vol. 242, No. 12, pp. 2933-2938.
Lewis et al., "Receptor-mediated folate uptake is positively regulated by disruption of actin cytoskeleton," Cancer Res. 58(14): 2952-2956 (1998).
Li et al, "Targeted delivery of antisense oligodeoxynucleotides by LPDII," J. Liposome Res. 7(1): 63 (1997).
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," J. Org. Chem. 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.

Low P.S. et al., "Folate Receptor-Targeted Drugs for Cancer and Inflammatory Diseases," Adv Drug Deliv Rev, 2004;56(8):1055-238.
Lu et al., "Folate-targeted enzyme prodrug cancer therapy utilizing penicillin-V amidase and a doxorubicin prodrug," J. Drug Target, 7(1): 43-53 (1999).
Lu, J. Y. and Low, P. S., "Folate targeting of haptens to cancer cell surfaces mediates immunotherapy of syngeneic murine tumors," Cancer Immunol Immunother, 51: 153-162 (2002).
Lu, J. Y. and Low, P. S., "Folate-mediated delivery of macromolecular anticancer therapeutic agents," Adv. Drug Del Rev, 2002; 54(5): 675-693.
Luo et al., "Efficient syntheses of pyrofolic acid and pteroyl azide, reagents for the production of carboxyl-differentiated derivatives of folic acid," J. Am. Chem. Soc., 119: 10004-10013 (1997).
Mack D.O. et al., "The Carboxylation Activity of Vitamin K Analogs with Substitutions at Position 2, 3, or 5," Journal of Biological Chemistry, 1979; vol. 254, pp. 2656-2664.
Mancuso A.J. et al., "Activated Dimethyl Sulfoxide: Useful Reagents for Synthesis," Synthesis, 1981, pp. 165-184.
Mathais et al., "Receptor-mediated targeting of 67Ga-deferoxamine-folate to folate-receptor-positive human KB tumor xenografts," Nucl Med Biol, 26(1): 23-25 (1999).
Mathais et al., "Synthesis of [(99m)Tc]DTPA-folate and its evaluation as a folate-receptor-targeted radiopharmaceutical," Bioconjug Chem, 11(2): 253-257 (2000).
Mathias et al., "Indium-111-DTPA-Folate as a potential folate-receptor-targeted radiopharmaceutical," J. Nucl. Med., 39(9): 1579-1585 (1998).
Mathias et al., "Tumor-Selective Radiopharmaceutical Targeting Via Receptor-Mediated Endocytosis of Gallium-67-Deferoxamine-Folate," J. Nucl. Med, 37(6): 1003-1008 (1996).
Mathias, C. J., "A kit formulation for preparation of [(111)In]In-DTPA-folate, a folate-receptor-targeted radiopharmaceutical," Nucl. Med. Biol., 25(6): 585-587 (1998).
Matsui et al., "Studies on mitomycins. III. The synthesis and properties of mitomycin derivatives," J Antibiot, 21: 189-198 (1968).
Kamao M. et al., "Determination of Plasma Vitamin K by High Performance Liquid Chromatography with Fluorescence Detection Using Vitamin K Analogs as Internal Standards," Journal of Chromatography B, 2005; vol. 816, pp. 41-48.
McAlinden TP et al., "Synthesis and Biological Evaluation of a Fluorescent Analogue of Folic Acid," Biochemistry, 1991; 30: 5674-81.
McHugh M et al., "Demonstration of a High Affinity Folate Binder in Human Cell Membranes and Its Characterization in Cultured Human KB Cells," J Biol Chem, 1979; 254(22):11312-8.
Melani et al., "Targeting of interleukin 2 to human ovarian carcinoma by fusion with a single-chain Fv of antifolate receptor antibody," Cancer Res. 58(18): 4146-4154 (1998).
Melby, E.L. et al, "Entry of Protein Toxins in Polarized Epithelial Cells"; Cancer Research, 1993; 53: 1755-1760.
Mislick et al., "Transfection of folate-polylysine DNA complexes: evidence for lysosomal delivery," Bioconjug. Chem., 6(5): 512-515 (1995).
Mock D.M. et al., "Urinary Biotin Analogs Increase in Humans During Chronic Supplementation: the Analogs are Biotin Metabolites," Am J Physiol Endocrinol Metab, 1997; 272: E83-E85.
Morshed et al., "Folate transport proteins mediate the bidirectional transport of 5-methyltetrahydrofolate in cultured human proximal tubule cells," J. Nutr., 127(6): 1137-1147 (1997).
Nair et al., "Folate analogs altered in the C9-N10 bridge region. 14. 11-Oxahomofolic acid, a potential antitumor agent", Journal of Medical Chemistry, 23: 59-65 (1980).
Nair et al., "Folate analogs altered in the C9-N10 bridge region. 18. Synthesis and antitumor evaluation of 11-oxahomoaminopterin and related compounds," Journal of Medical Chemistry, 24: 1068-1073 (1981).
Nair et al., "Folate analogs altered in the C9-N10 bridge region: N10-tosylisohomofolic acid and N10-tosylisohomoaminopterin," Journal of Medical Chemistry, 21: 673-677 (1978).

(56) References Cited

OTHER PUBLICATIONS

Nair et al., "Folate analogs altered in the C9-N10 bridge region: 11-thiohomofolic acid," *Journal of Medical Chemistry*, 22: 850-855 (1979).
Nair et al., "Folate analogs. 20. Synthesis and antifolate activity of 1',2',3',4',5',6'-hexahydrohomofolic acid," *Journal of Medical Chemistry*, 26: 135-140 (1983).
Nair et al., "Folate analogs. 21. Synthesis and antifolate and antitumor activities of N10-(cyanomethyl)-5,8-dideazafolic acid," *Journal of Medical Chemistry*, 26: 605-607 (1983).
Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).
Nair et al., "Folate analogues altered in the C9-N10 bridge region. 10-Oxafolic acid and 10-oxaaminopterin," *Journal of Medical Chemistry*, 19: 825-829 (1976).
Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).
Neuzil J. et al., "Vitamin E Analogs: A New Class of Multiple Action Agents with Anti-Neoplastic and Anti-Atherogenic Activity," *Apoptosis*, 2002; vol. 7, pp. 179-187.
Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.
Nimmo-Smirth R.H. et al., "Some Effects of 2-deaminopteroylglutamic Acid upon Bacterial Growth," *J. Gen. Microbial.*, 1953; 9: 536-544.
Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.
Nomura, Makoto et al., "Development of an Efficient Intermediate a-[2-(Trimethylsilyl)ethoxy]-2-N-[2-(trimethylsilyl)ethoxycarbonyl]folic Acid, for the Synthesis of Folate (y)-Conjugates, and Its Application to the Synthesis of Folate-Nucleoside Congugates," *Journal of Organic Chemistry*, 2000, vol. 65, pp. 5016-5021.
Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.
Oatis et al., "Synthesis of quinazoline analogues of folic acid modified at position 10," *Journal of Medical Chemistry*, 20: 1393-1396 (1977).
Olsnes S. et al., "Immunotoxins-entry into cells and mechanisms of action," *Immunology Today*, 1989; vol. 10, No. 9, pp. 291-295.
Patrick et al., "Folate Receptors as Potential Therapeutic Targets in Choroid Plexus Tumors of Sv40 Transgenic Mice," *J. Neurooncol,.* 32(2): 111-123 (1997).
Patrick et al., "Intracerebral bispecific ligand-antibody conjugate increases survival of animals bearing endogenously arising brain tumors," *Int. J. Cancer*, 78(4): 470-79 (1998).
Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Prabhu V. et al., "Arabidopsis dihydropteroate synthase: general properties and inhibition by reaction product and sulfonamides," *Phytochem.*, 1997; 45(1): 23-27.
Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Punj, V. et al., "Effect of Vitamin D Analog (1α Hydroxy D5) Immunoconjugated to Her-2 Antibody on Breast Cancer," *Int. J. Cancer*, 2004; 108: 922-929.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res.*, 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Remington: The Science & Practice of Pharmacy, 21th Edition (Lippincott Williams & Wilkins, 2005).
Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.
Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4. 3'-Ethyl- and 3'- isopropylfolic acids," *Journal of Medical Chemistry*, 17: 219-222 (1974).
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Roy et al., "Targeting T cells against brain tumors with a bispecific ligand-antibody conjugate," *Int. J. Cancer* 76(5): 761-66 (1998).
Sadasivan et al., "The complete amino acid sequence of a human folate binding protein from KB cells determined from the cDNA," *J. Biol. Chem.*, 1989; 264: 5806-5811.
Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.

(56) References Cited

OTHER PUBLICATIONS

Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Toffoli et al., "Overexpression of folate binding protein in ovarian cancers," *Int. J. Cancer* 74(2): 193-198 (1997).
Toraya T. et al., "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh A. et al., "Temperature-sensitive differential affinity of TRAIL for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.
Wiener et al., "Targeting dendrimer-chelates to tumors and tumor cells expressing the high-affinity folate receptor," *Invest. Radiol.* 32(12): 748-54 (1997).
Wu M. et al., "Clustering of GPI-anchored folate receptor independent of both cross-linking and association with caveolin," *J. Membr. Biol.* 159(2): 137-147 (1997).
Zimmer H. et al., "Potential anticancer agents V., Synthesis of folic acid and pteroic acid analogs derived of caffeine and theophylline," *Arzneimittelforschung*, 1966, 16(4), pp. 541-545.
Zimmerman, J., "Folic acid transport in organ-cultured mucosa of human intestine. Evidence for distinct carriers," *Gastroenterol.* 99(4): 964-972 (1990).
Angier, R. B., et al., "Pteroic Acid Analogs Containing Arsenic," J. American Chem. Soc., vol. 76, 1954, pp. 902-904.

(56) References Cited

OTHER PUBLICATIONS

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," Journal of Chromatography A, 1994; vol. 659(1): 185-189 (abstract only).

Wikipedia, Derivative (Chemistry), http://en.wikipedia.org/wiki/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, List of Purification Methods in Chemistry, http://en.wikipedia.org/wiki/List_of_purification_methods_in_chemistry, downloaded Dec. 16, 2009.

Wikipedia, Solution, http://en.wikipedia.org/wiki/Solution, downloaded Dec. 17, 2009.

Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid Its Derivatives" J. Org. Chem. 2000;65:1562-1565.

Carl et al. "A novel connector linkage applicable in prodrug design" J. Med. Chem. 1981;24(5):479-480.

Coney et al. "Cloning of a tumor-associated antigent: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Synthesis: A Guide to Successful Synthesis Design," Wiley-VCH, Weinheim, 2005, p. ix of preface.

Forgac. "Structure and function of vacuolar class of ATP-driven pumps" Physiological Rev. 1989; 69(3): 765-795.

Garrett et al. "Synthesis and characterisation of polyamine-poly-(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance"In Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Ke et al. "Targeting the Tumor-Associated Folate Receptor with a 111-IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

Kemp et al. "New Protective Groups for Peptide Synthesis-I the Bic Group Base and Solvent Lability of the 5-B enzi soxazolymethyl eneoxycarbonyl amino function" Tet. Lett. 1975;52:4625-4628.

Kutsky RJ. Handbook of Vitamins, Minerals, and Hormones, 2 Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.

Mehvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor-Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. Invest. 1971; 50(3):719-726.

Selhub et al. "The folate binding protein of rat kidney. Purification, properties, and cellular distribution" J. Biol. Chem. 1984;259(10):6601-6606.

Selhub et al. "Renal folate adsorption and the kidney folate binding protein I. Urinary Clearance studies" Am. J Physiol. 252:F750-F756.

Selhub et al. "Renal folate adsorption and the kidney folate binding protein II. Microinfusion studies" Am. J. Physiol. 252:F757-F760.

Sirotnak. "Obligate genetic expression in tumor cells of a fetal membrane property mediating "Folate" transport: biological significance and implications for improved therapy of human cancer" Cancer Res., 1985;45(9):3992-4000.

Stein et al. "Normal tissue reactivity of four anti-tumor monoclonal antibodies of clinical interest" Int. J. Cancer 1991;47(2):163-169.

Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.

Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.

Toffoli et al. "Expression of folate binding protein as a prognostic factor for response to platinum-containing chemotherapy and survival in human ovarian cancer" Int. J. Cancer (Pred. Oncol) 1998; 79:121-126.

Westerhof et al. "Membrane transport of natural folates and antifolate compounds in murine L1210 Leukemia cells: role of carrier-and receptor mediated transport systems" Cancer Res. 1991;51:5507-5513.

Williams et al. "Renal tubular transport of folic acid and methotrexate in the monkey" Am. J. Physiol 1982; 242(5):F484-490.

Weygand, et al., Chemishe. Berichte (1950) 83, 460-467.

(56) References Cited

OTHER PUBLICATIONS

Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.

Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.

Bukanov Nikolay, O. et al., "Long-Lasting Arrest of Murine Polycystic Kidney Disease With CDK Inhibitor Roscovitine", Dec. 14, 2006; *Nature*; vol. 444; pp. 949-952.

Hay, Nissim, et al., "Upstream and Downstream of mTOR", 2004, *Genes & Development*, vol. 18, No. 16, pp. 1926-1945.

Kennedy, Michael D., et al., "Evaluation of Folate Conjugate Uptake and Transport by the Choroid Plexus of Mice", (May 2003), vol. 20, No. 5, pp. 714-719.

Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.

Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.

Piontek, Klaus B., et al. "A Functional Floxed Allele of *Pkd1* that Can Be Conditionally Inactivated In Vivo", *J. Am. Soc. Nephrol.* vol. 15, pp. 3035-3043.

Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS.* vol. 103, No. 14, pp. 5466-5471.

Ke Cy et al., "Folate-Receptor-Targeting of In-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Antony, "Folate receptors: reflections on a personal odysssey and a perspective on unfolding truth," Advanced Drug Delivery Reviews, 2004; vol. 56: 1059-66.

Lu et al., "Folate receptor-targeted immunotherapy of cancer: mechanism and therapeutic potential," Advanced Drug Delivery Reviews, 2004; vol. 56: 1161-76.

Roy et al., "Folate-mediated targeting of T cells to tumors," Advanced Drug Delivery Reviews, 2004; vol. 56: 1219-31.

Ke et al., "Folate-receptor-targeted radionuclide imaging agents," Advanced Drug Delivery Reviews, 2004; vol. 56: 1143-60.

Gabizon et al., "Tumor cell targeting of liposome-entrapped drugs with phospholipid-anchored folic acid-PEG Conjugates," Advanced Drug Delivery Reviews, 2004; vol. 56: 1177-92.

Zhao et al., "Tumor-selective targeted delivery of genes and antisense oligodeoxyribonucleotides via the folate receptor," Advanced Drug Delivery Reviews, 2004; vol. 56: 1193-1204.

Paulos CM et al., "Ligand Binding and Kinetics of Folate Receptor Recycling in Vivo: Impact on Receptor-Mediated Drug Delivery," Molecular Pharmacology, 2004; 66:1406-1414.

Griesser UJ, "The Importance of Solvents," in Polymorphism in the Pharmaceutical Industry, Hilfiker ed., 2006; p. 211-230.

Wikipedia, Structural analog, http://en.wikipedia.org/wiki/Structural_analog, downloaded Apr. 7, 2009.

Wikipedia, Functional analog, http://en.wikipedia.org/wiki/Functional_analog, downloaded Apr. 7, 2009.

Wikipedia, Folic acid, http://en.wikipedia.org/wiki/Folic_acid, downloaded Apr. 7, 2009.

Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.

Wang, Zhiyong, et al. "Structure-activity and High-content Imaging Analyses of Novel Tubulysins." Chemical biology & drug design 70(2): 75-86 (2007).

Patterson, Andrew W., et al. "Design, synthesis, and biological properties of highly potent tubulysin D analogues." Chemistry—A European Journal 13(34): 9534-9541 (2007).

Steinmetz, Heinrich, et al. "Isolation, crystal and solution structure determination, and biosynthesis of tubulysins—powerful inhibitors of tubulin polymerization from myxobacteria." Angewandte Chemie International Edition 43(37): 4888-4892 (2004).

March, Jerry. Advanced organic chemistry: reactions, mechanisms, and structure. vol. 4. New York: McGraw-Hill, 1968, p. 362-363, 816, 885, 896.

Lopes, Francisca, Rui Moreira, and Jim Iley. "Acyloxymethyl as a drug protecting group. Part 5.1 Kinetics and mechanism of the hydrolysis of tertiary N-acyloxymethylsulfonamides." J. Chem. Soc., Perkin Trans. 2, vol. 3: 431-440 (1999).

Churlaud, Carine, et al., "Novel 4-(Trimethylsilyl)aminoalkanes and 4-(Trimethylsilyl)aminoalk-2-enes, via a 1,5-Hydride Shift, in the Reaction of r-Unsaturated Silanes with Aminomethylbenzotriazoles," Organometallics, 18(21): 4270-4274.

Peltier, Hillary M., et al. "The total synthesis of tubulysin D." Journal of the American Chemical Society 128(50): 16018-16019 (2006).

Sasse, F., et al. "Tubulysins, new cytostatic peptides from myxobacteria acting on microtubuli. Production, isolation, physico-chemical and biological properties," J Antibiot 53:879-885 (2000).

Rose, "Taxol-based combination chemotherapy and other in vivo preclinical antitumor studies," J Natl Cancer Inst Monogr 15:47-53 (1993).

Khalil, M., et al., "Mechanism of Action of Tubulysin, an Antimitotic Peptide from Myxobacteria," ChemBioChem. 7(4):678-683 (2006).

Kaur, G., et al., "Biological evaluation of tubulysin A: a potential anticancer and antiangiogenic natural product," Biochem. J. 396, 235-242 (2006).

Domling, A., et al., "Myxobacterial epothilones and tubulysins as promising anticancer agents," Mol. Diversity, 9:141-147 (2005).

Pathak, et al. "Enzymatic protecting group techniques in organic synthesis," Stereosel. Biocatal. 2000, pp. 775-797.

Remington: The Science and Practice of Pharmacy, $21^{st}$ ed., (2005).

Pando, O., et al, "First Total Synthesis of Tubulysin B." Org. Lett., 11(24): 5567-5569 (2009).

G. Hofle, G., et al., "Semisynthesis and degradation of the tubulin inhibitors epothilone and tubulysin," Pure Appl. Chem. 75:167-178 (2003).

Raghavan, Bhooma, et al. "Cytotoxic Simplified Tubulysin Analogues," J. Med. Chem. 51:1530-1533 (2008).

PCT Search Report for PCT/EP2003/011603, completed Feb. 11, 2004.

PCT Search Report and Written Opinion for US2008/080948, completed Dec. 4, 2008.

Wu, Shih Hsiung, Zhi Wei Guo, and Charles J. Sih. "Enhancing the enantioselectivity of Candida lipase-catalyzed ester hydrolysis via noncovalent enzyme modification." Journal of the American Chemical Society 112(5): 1990-1995 (1990).

Patterson, Andrew W., Hillary M. Peltier, and Jonathan A. Ellman. "Expedient synthesis of N-methyl tubulysin analogues with high cytotoxicity." The Journal of organic chemistry 73(12): 4362-4369 (2008).

Lee et al., "BMS-247550: a novel epothilone analog with a mode of action similar to paclitaxel but possessing superior antitumor efficacy" Clin Cancer Res 7:1429-1437 (2001).

PCT Search Report and Written Opinion for PCT/US2011/046797, completed Dec. 23, 2011.

(56) References Cited

OTHER PUBLICATIONS

Speckamp, et al., "New Developments in the Chemistry of N-Acyliminium Ions and Related Intermediates," Tetrahedron 56(24):3817-3856 (2000).
European Search Report prepared for corresponding European Application Serial No. 08841521.1, mailed Jul. 18, 2011.
PCT Search Report and Written Opinion for PCT/EP2003/011603, completed Feb. 11, 2011.

* cited by examiner

TUBULYSINS AND PROCESSES FOR PREPARING

CROSS-REFERENCE TO RELATED APPLICATIONS

This application is a continuation application of U.S. patent application Ser. No. 12/739,579, filed Apr. 23, 2010, which is a U.S. national application under 35 U.S.C. §371(b) of International Application Ser. No. PCT/US2008/080948 filed Oct. 23, 2008, which claims the benefit under 35 U.S.C. §119(e) of U.S. Provisional Application Ser. No. 60/982,595, filed Oct. 25, 2007, and U.S. Provisional Application Ser. No. 61/036,176, filed Mar. 13, 2008, the disclosures of which are hereby incorporated herein by reference.

TECHNICAL FIELD

The invention described herein pertains to tubulysins and tubulysin analogs, and processes for preparing tubulysins and tubulysin analogs.

BACKGROUND

Tubulysins are a group of powerful inhibitors of tubulin polymerization. Tubulysins are useful in treating diseases and disease states that include pathogenic cell populations, such as cancer. Generally, tubulysins are linear tetrapeptides consisting of N-methyl pipecolic acid (Mep), isoleucine (Ile), an unnatural aminoacid called tubuvalin (Tuv), and either an unnatural aminoacid called tubutyrosine (Tut, an analog of tyrosine) or an unnatural aminoacid called tubuphenylalanine (Tup, an analog of phenylalanine), as shown in the following table:

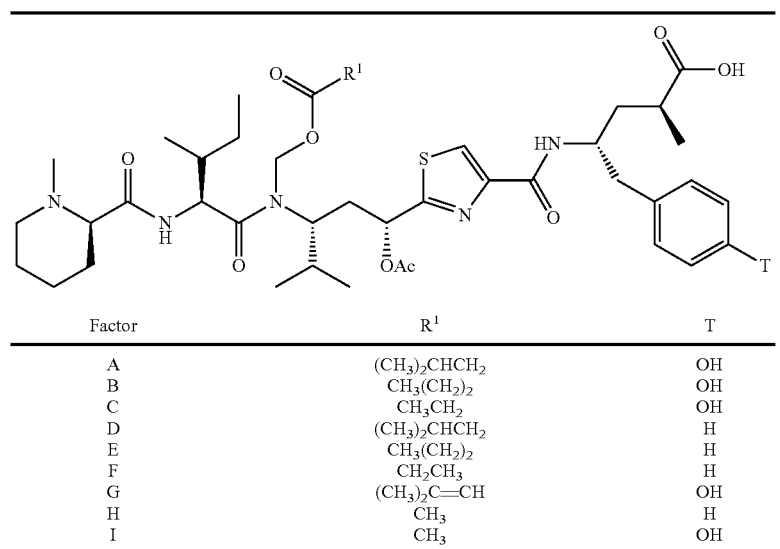

| Factor | R$^1$ | T |
|---|---|---|
| A | (CH$_3$)$_2$CHCH$_2$ | OH |
| B | CH$_3$(CH$_2$)$_2$ | OH |
| C | CH$_3$CH$_2$ | OH |
| D | (CH$_3$)$_2$CHCH$_2$ | H |
| E | CH$_3$(CH$_2$)$_2$ | H |
| F | CH$_2$CH$_3$ | H |
| G | (CH$_3$)$_2$C=CH | OH |
| H | CH$_3$ | H |
| I | CH$_3$ | OH |

Two particular species of mycobacteria synthesize tubulysins in high titer during fermentation. However, each species generally synthesizes a mixture of tubulysin factors, and that mixture differs between each of those mycobacteria species. For example, one species, *Archangium gephyra*, produces as the main component factors tubulysins A, B, C, G, and I, each of which may be identified by its including the Tut residue. In contrast, another species, *Angiococcus disciformis*, produces as the main component factors tubulysins D, E, F, and H, each of which may be identified by its including the Tup residue.

Such bacterial fermentations are convenient sources of tubulysins. However, because the mycobacteria produce only certain tubulysins, and/or mixtures of tubulysins, processes are needed for interconverting those tubulysins to the desired factors for medicinal and pharmacological uses. In addition, processes are needed for preparing novel tubulysins, tubulysin analogs, and tubulysin derivatives for medicinal and pharmacological uses.

SUMMARY OF THE INVENTION

Described herein are processes for preparing tubulysins. Also described herein are analogs and derivatives of tubulysins. In one embodiment, processes are described for preparing one or more tubulysins from a mixture of tubulysins, such as a mixture of tubulysins produced by fermentation or some other process. In another embodiment, processes are described herein for preparing a mixture of tubulyins from one or more tubulysins. In another embodiment, processes are described herein for converting one tubulysin into another tubulysin. In another embodiment, processes are described herein for converting one or more, or a mixture of tubulysins into one or more, or a mixture of tubulysin analogs. It is to be understood that as used herein, the term tubulysin refers both collectively and individually to the naturally occurring tubulysin, and the analogs and derivatives of tubulysins described herein, or that may be prepared from the processes described herein.

In another embodiment, novel tubulysins, tubulysin analogs, and tubulysin derivatives are described herein along with processes for preparing such novel tubulysins, tubulysin analogs, and tubulysin derivatives. In one embodiment, the processes include treating one or more tubulysins with an acid to prepare an intermediate. In another embodiment, the processes include the step of subsequently reacting the intermediate with a reagent to prepare a mixture of tubulysins from a different mixture of tubulysins, a single tubulysin from a mixture of tubulysins, a mixture of tubulysins from a single tubulysin, or a single tubulysins from a different tubulysin.

In one embodiment of the processes described herein, the intermediate is a compound of formulae (1a), (1b), or (1c):

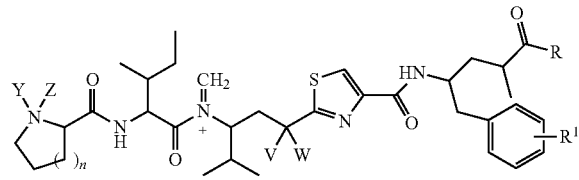
(1a)

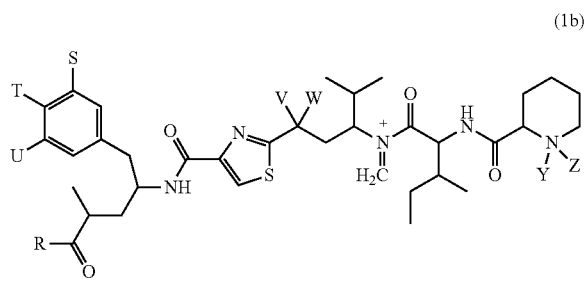
(1b)

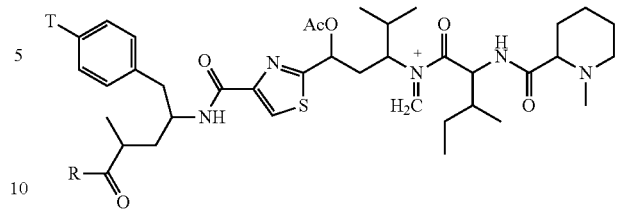
(1c)

wherein R, R¹, S, T, U, V, W, Y, and Z are as described hereinbelow in the various embodiments, aspects, and variations thereof.

It is understood that intermediate compounds of formulae (1a), (1b), and (1c) may form salts, such as salts with the residual acid conjugate base. In addition, it is understood that iminium intermediates, such as those of formulae (1a), (1b), and (1c) may also be in equilibrium with the corresponding acyl aminal, where the residual acid conjugate base adds to the iminium intermediate. It is further appreciated that the iminium intermediates may form solvates or hydrates, each of which may be in equilibrium with the iminium intermediates. In any case, without being bound by theory, it is believed that nucleophiles such as RCN, RXH and the corresponding anions and salts thereof react with iminium intermediates regardless of whether the iminium is in a salt, hydrate, solvate or acylaminal form to prepare the compounds described herein, such as the compounds of formulae (2a), (2b), and (2c), respectively:

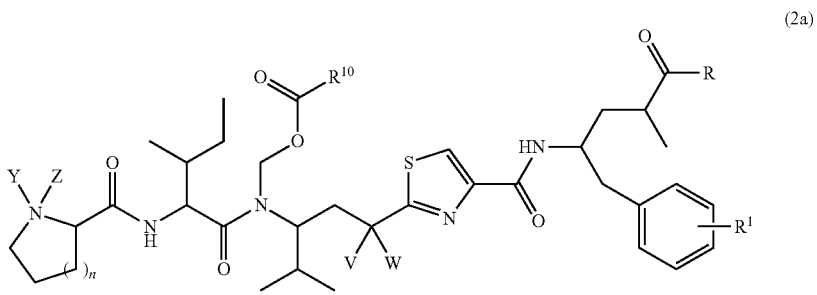
(2a)

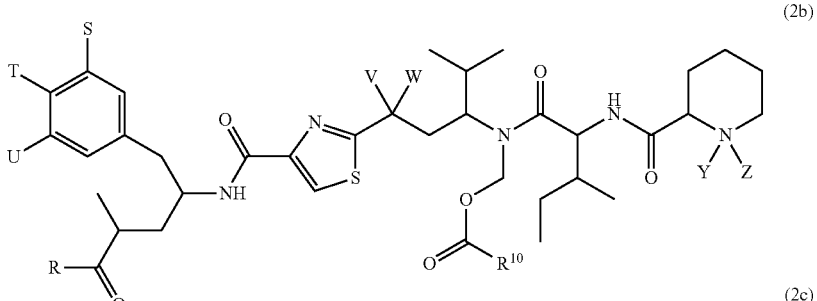
(2b)

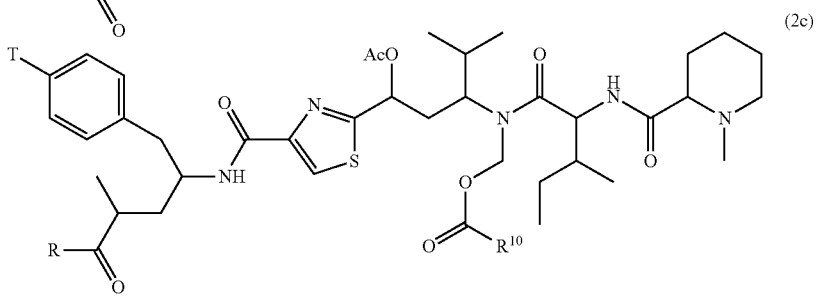
(2c)

wherein R, $R^1$, $R^{10}$, S, T, U, V, W, Y, and Z are as described hereinbelow in the various embodiments, aspects, and variations thereof.

DETAILED DESCRIPTION

Described herein are processes for converting a single tubulysin or a mixture of tubulysin compounds into a single tubulysin compound or a different mixture of tubulysin compounds. In one embodiment, tubulysins described herein refer generally to tetrapeptide compounds of the formula

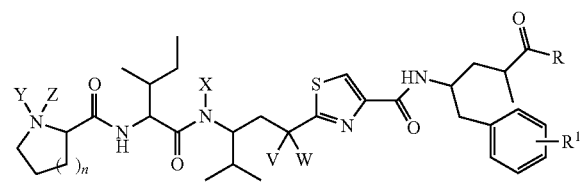

and pharmaceutical salts thereof, where n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and $OR^6$, where $R^6$ is optionally substituted aryl, $C(O)R^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative.

In one variation, Z is methyl. In another variation, $R^1$ is H. In another variation, $R^1$ is $OR^6$ at C(4), where $R^6$ is H, alkyl, or $COR^7$. In another variation, V is H, and W is $OC(O)R^3$.

Illustrative leaving groups include, but are not limited to halides, sulfonates, such as triflates, and the like, optionally substituted phenoxy, such as pentafluorophenoxy and the like, intermediates formed from ester forming or amide forming reagents, such as isobutyl chloroformate, DCC, HOBt, EDC, PyBOP, BOP, BOP-Cl, and the like.

Illustrative carboxylic acid derivatives include, but are not limited to, esters, amides, imides, acylhydrazides, nitriles, and optionally substituted variations thereof.

In another embodiment, tubulysins of the following general formula are described

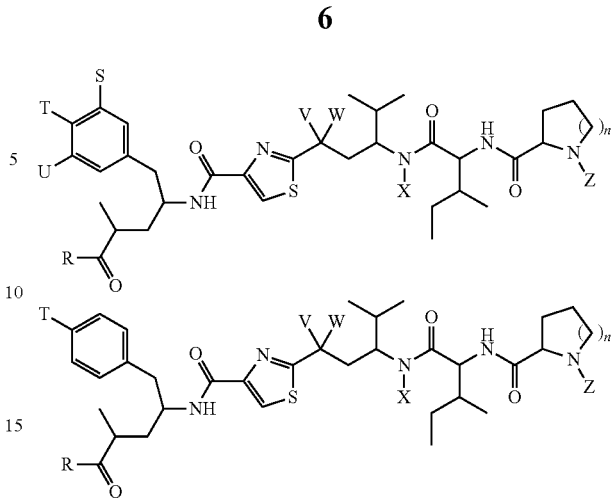

and pharmaceutical salts thereof, where n is 1-3;

V is H, $OR^2$, or halo, and W is H, $OR^2$, or alkyl, where $R^2$ is independently selected in each instance from H, alkyl, or $C(O)R^3$, where $R^3$ is alkyl, alkenyl or aryl, providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl;

Z is alkyl or $C(O)R^4$, where $R^4$ is alkyl, $CF_3$, or aryl;

T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation, or $R^6$ is a phenol protecting group, or a prodrug moiety;

S and U are each independently selected from the group consisting of H, halo, nitro, cyano, alkyl, haloalkyl, alkoxy, and haloalkoxy; and R is OH or a leaving group, or R forms a carboxylic acid derivative.

In one embodiment, natural tubulysins, and the corresponding analogs and derivatives thereof are described. Such natural tubulysins are generally linear tetrapeptides consisting of N-methyl pipecolic acid (Mep), isoleucine (Ile), an unnatural aminoacid called tubuvalin (Tuv), and either an unnatural aminoacid called tubutyrosine (Tut, an analog of tyrosine) or an unnatural aminoacid called tubuphenylalanine (Tup, an analog of phenylalanine). In another embodiment, naturally occurring tubulysins, and analogs and derivatives thereof, of the following general formula are described

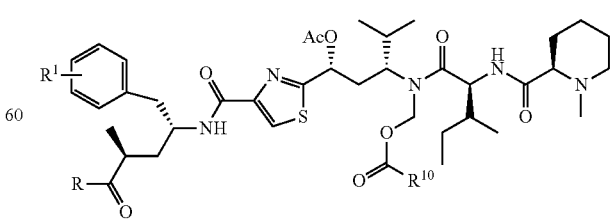

and pharmaceutical salts thereof, where R, $R^1$, and $R^{10}$ are as described in the various embodiments herein.

In one embodiment, a first tubulysin, or alternatively a mixture of tubulysins, is converted into a second tubulysin by preparing an intermediate compound of formula (1a), wherein n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and $OR^6$, where $R^6$ is optionally substituted aryl, $C(O)R^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative. The intermediate is prepared by mixing a tubulysin or mixture of tubulysins of formula (2b) with an acid under substantially anhydrous conditions:

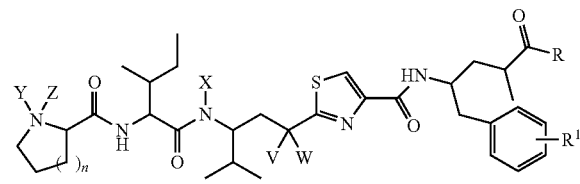

and pharmaceutical salts thereof, where n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and $OR^6$, where $R^6$ is optionally substituted aryl, $C(O)R^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative.

The intermediate compound of formula (1a) is then treated with a compound of formula $R^{10}CO_2H$, where $R^{10}$ is not the same as $R^{10}$ present in the first tubulysin used to prepare the second compound of formula (2a).

In one variation, Z is methyl. In another variation, $R^1$ is H. In another variation, $R^1$ is $OR^6$ at C(4), where $R^6$ is H, alkyl, or $COR^7$. In another variation, V is H, and W is $OC(O)R^3$. In another variation, R is OH. In another variation, R forms an ester derivative. In another variation, R forms an amide derivative. In another variation, R forms an acylhydrazide derivative, such as the compound formed from hydrazine.

In another embodiment, a first tubulysin, or alternatively a mixture of tubulysins, is converted into a second tubulysin by preparing an intermediate compound of formula (1b), wherein V is H, $OR^2$, or halo, and W is H, $OR^2$, or alkyl, where $R^2$ is independently selected in each instance from H, alkyl, or $COR^3$, where $R^3$ is alkyl, alkenyl or aryl, providing that $R^2$ is not H when both V and W are $OR^2$; or V and W are taken together with the attached carbon to form a carbonyl; Z is $CH_3$ or $COR^4$, and Y is absent; or Z is $CH_3$ and, Y is O; where $R^4$ is alkyl, $CF_3$ or aryl; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH. The intermediate is prepared by mixing a tubulysin or mixture of tubulysins of formula (2b) with an acid under substantially anhydrous conditions:

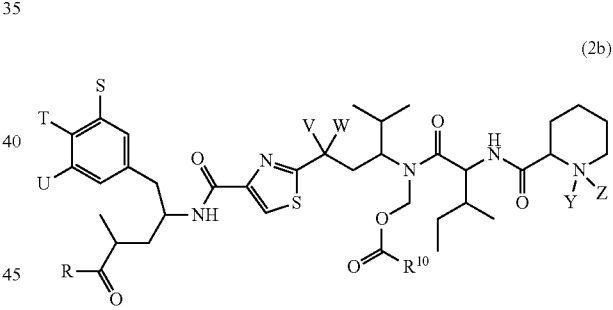

wherein $R^{10}$ is H, alkyl, alkenyl, cycloalkyl, aryl, and arylalkyl, each of which is optionally substituted; V is H, $OR^2$, or halo, and W is H, $OR^2$, or alkyl, where $R^2$ is independently selected in each instance from H, alkyl, or $COR^3$, where $R^3$ is alkyl, alkenyl, cycloalkyl, aryl or arylalkyl, each of which is optionally substituted, providing that $R^2$ is not H when both V and W are $OR^2$; or V and W are taken together with the attached carbon to form a carbonyl; Z is $CH_3$ or $COR^4$, and Y is absent; or Z is $CH_3$ and, Y is O; where $R^4$ is alkyl, $CF_3$ or aryl; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH. The intermediate compound of formula (1b) is then treated with a compound of formula R¹⁰CO₂H, where R¹⁰ is not the same as R¹⁰ in the first tubulysin to prepare the second compound of formula (2b).

In another embodiment, a first tubulysin or a mixture of tubulysins is converted into a second tubulysin by preparing an intermediate compound of formula (1c), wherein T is H or OH. The intermediate is prepared by mixing a tubulysin or mixture of tubulysins of formula (2c) with an acid under substantially anhydrous conditions:

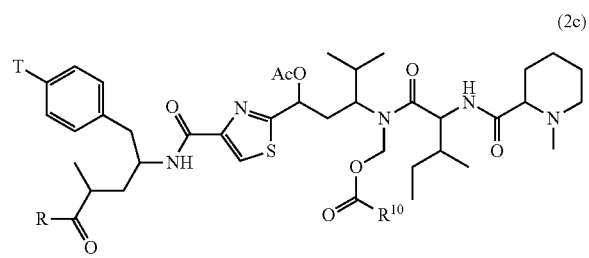

(2c)

wherein T is H or OH and R¹⁰ is H, alkyl, alkenyl, cycloalkyl, aryl, and arylalkyl, each of which is optionally substituted, or the corresponding carboxylic acid derivative thereof, where R is other than OH. The intermediate compound of formula (1c) is then treated with a compound of formula R¹⁰CO₂H where R¹⁰ is not the same as R¹ present in the starting tubulysin used to prepare the second compound of formula (2c).

In each of the foregoing embodiments, it is understood that in certain configurations, the tubulysins may instead be converted into different mixtures of tubulysins rather than a single tubulysin. In such embodiments, a single starting tubulysin, or mixture of tubulysins, may be first converted into a common intermediate compound or a mixture of intermediate compounds of formulae (1a), (1b), or (1c), then those intermediate compounds are reacted with a mixture of carboxylic acids to provide the desired mixture of tubulysins. For example, if a mixture of tubulysins B and C, or the corresponding analogs or derivatives thereof, is desired, a single starting tubulysin, such as tubulysin A, or the corresponding analog or derivative thereof, or alternatively a mixture of tubulysins, may be first converted into the corresponding compound of formulae (1a), (1b), or (1c), wherein T is OH, then reacted with a mixture of carboxylic acids, such as butanoic acid and propanoic acid, corresponding to the appropriate groups on tubulysin B and C, respectively. It is appreciated that a statistical mixture may result based on the relative proportion of carboxylic acids used in the second step. Alternatively, it is also appreciated that kinetic and thermodynamic factors may influence the final proportion of tubulysins obtained in the second step and thus a statistical mixture of tubulysins based on the ratio of carboxylic acids will not result. In either case, it is understood that routine optimization of the relative ratios of carboxylic acid mixtures will afford the desired mixture of tubulysins from common intermediates of formulae (1a), (1b), and (1c).

In another embodiment, intermediate compound of formula (1b) can be treated with a compound of formula R⁹QH or the anion prepared therefrom to give a compound of the following formula:

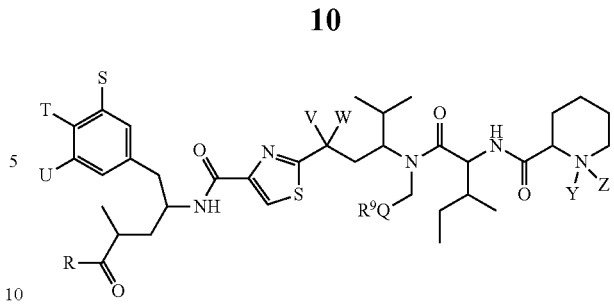

wherein Q is —N—, —O—, or —S—; R⁹ is H, alkyl, alkenyl, cycloalkyl, aryl, or arylalkyl, each of which is optionally substituted, or R⁹ is C(O)R²⁰, S(O)₂R²⁰, or P(O)(OR²⁰)₂; where R²⁰ is independently selected in each instance from the group consisting of H, alkyl, alkenyl, cycloalkyl, aryl, and arylalkyl, each of which is optionally substituted, or R²⁰ is a metal cation; V is H, OR², or halo, and W is H, OR², or alkyl, where R² is independently selected in each instance from H, alkyl, or COR³, where R³ is alkyl, alkenyl, cycloalkyl, aryl or arylalkyl, each of which is optionally substituted, providing that R² is not H when both V and W are OR²; or V and W are taken together with the attached carbon to form a carbonyl Z is CH₃ or COR⁴, and Y is absent; or Z is CH₃ and, Y is O; where R⁴ is alkyl, CF₃ or aryl; T is H or OR⁶, where R⁶ is H, alkyl, aryl, COR⁷, P(O)(OR⁸)₂, or SO₃R⁸, where R⁷ and R⁸ are independently selected in each instance from H, alkyl, alkenyl, cycloalkyl, heterocyclyl, aryl, and arylalkyl, each of which is optionally substituted, or R⁸ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (1c) can be treated with a compound of formula R⁹QH or an anion thereof to give a compound of the following formula:

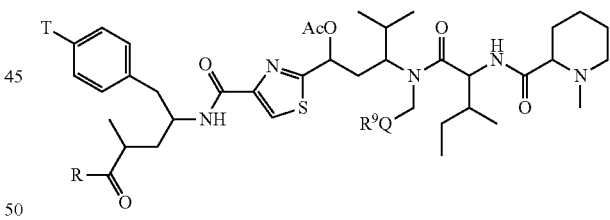

wherein Q is —N—, —O—, or —S—; R⁹ is H, alkyl, alkenyl, cycloalkyl, aryl, or arylalkyl, each of which is optionally substituted, or R⁹ is C(O)R²⁰, S(O)₂R²⁰, or P(O)(OR²⁰)₂; where R²⁰ is independently selected in each instance from the group consisting of H, alkyl, alkenyl, cycloalkyl, aryl, and arylalkyl, each of which is optionally substituted, or R²⁰ is a metal cation: and T is H or OH, or the corresponding carboxylic acid derivative thereof, where R is other than OH.

It is to be understood that the corresponding compounds of formula (2a) may be similarly prepared via the corresponding intermediate of formula (1a) and R⁹QH.

In another embodiment, intermediate compound of formula (1b) can be treated with a nitrile compound, R²¹CN, to give a compound of the following formula:

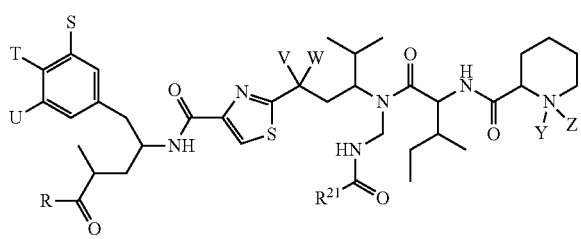

wherein $R^{21}$ is alkyl, alkenyl, cycloalkyl, aryl, or arylalkyl, each of which is optionally substituted; V is H, $OR^2$, or halo, and W is H, $OR^2$, or alkyl, where $R^2$ is independently selected in each instance from H, alkyl, or $COR^3$, where $R^3$ is alkyl, alkenyl, cycloalkyl, aryl or arylalkyl, each of which is optionally substituted, providing that $R^2$ is not H when both V and W are $OR^2$; or V and W are taken together with the attached carbon to form a carbonyl Z is $CH_3$ or $COR^4$, and Y is absent; or Z is $CH_3$ and, Y is O; where $R^4$ is alkyl, $CF_3$ or aryl; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (1c) can be treated with a nitrile compound, $R^{21}CN$, to give a compound of the following formula:

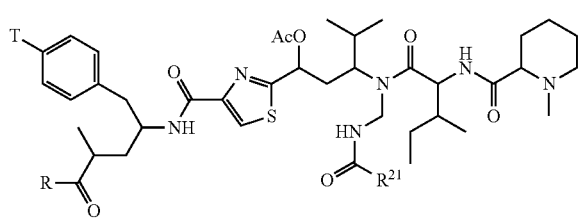

wherein $R^{21}$ is alkyl, alkenyl, cycloalkyl, aryl, or arylalkyl, each of which is optionally substituted and T is H or OH, or the corresponding carboxylic acid derivative thereof, where R is other than OH.

It is to be understood that the corresponding compounds of formula (2a) may be similarly prepared via the corresponding intermediate of formula (1a) and $R^{21}CN$.

In another embodiment, intermediate compound of formula (1b) can be treated with an alkenylsilane of formula $R^{22}(TMS)CCH_2$ to give a compound of the following formula:

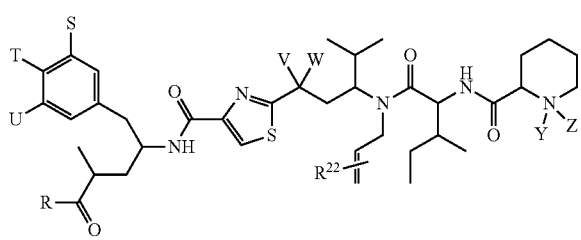

wherein $R^{22}$ is alkyl, alkenyl, cycloalkyl, aryl, or arylalkyl, each of which is optionally substituted; V is H, $OR^2$, or halo, and W is H, $OR^2$, or alkyl, where $R^2$ is independently selected in each instance from H, alkyl, or $COR^3$, where $R^3$ is alkyl, alkenyl, cycloalkyl, aryl or arylalkyl, each of which is optionally substituted, providing that $R^2$ is not H when both V and W are $OR^2$; or V and W are taken together with the attached carbon to form a carbonyl; Z is $CH_3$ or $COR^4$, and Y is absent; or Z is $CH_3$ and, Y is O; where $R^4$ is alkyl, $CF_3$ or aryl; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (1c) can be treated with an alkenylsilane of formula $R^{22}(TMS)CCH_2$ to give a compound of the following formula:

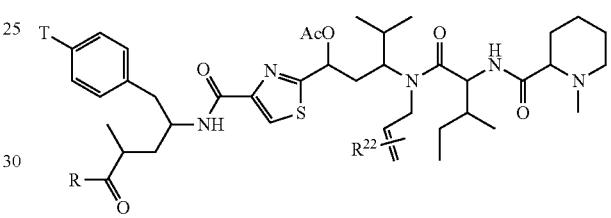

wherein $R^{22}$ is alkyl, alkenyl, cycloalkyl, aryl, or arylalkyl, each of which is optionally substituted; and T is H or OH, or the corresponding carboxylic acid derivative thereof, where R is other than OH.

It is to be understood that the corresponding compounds of formula (2a) may be similarly prepared via the corresponding intermediate of formula (1a) and $R^{22}(TMS)CCH_2$.

It is understood that in the preceding embodiments other olefins may form by isomerization, depending on the conditions of the reaction and the identity of $R^{22}$. For example, when $R^{22}$ is alkyl, it is appreciated that under the reaction conditions, the double bond can migrate to other carbon atoms along the alkenyl chain, including to form the terminal or ω-olefin.

In another embodiment, intermediate compound of formula (1b) is treated with a compound of formula $R^{23}C(O)CH_2R^a$ to give a compound of the following formula:

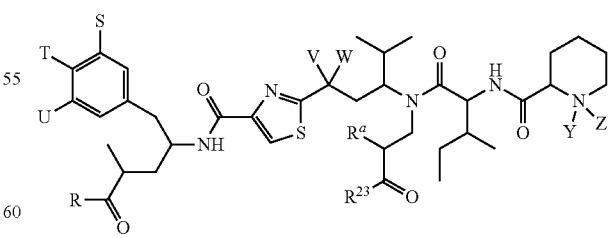

wherein $R^{23}$ is H, alkyl, alkenyl, cycloalkyl, aryl, or arylalkyl, each of which is optionally substituted; $R^a$ is $C(O)R^9$, $C(O)OR^9$ or CN; $R^9$ is selected from the group consisting of H, alkyl, alkenyl, cycloalkyl, aryl, and arylalkyl, each of which is optionally substituted; V is H, $OR^2$, or halo, and W is H, OR², or alkyl, where R² is independently selected in each instance from H, alkyl, or COR³, where R³ is alkyl, alkenyl, cycloalkyl, aryl or arylalkyl, each of which is optionally substituted, providing that R² is not H when both V and W are OR²; or V and W are taken together with the attached carbon to form a carbonyl; Z is CH₃ or COR⁴, and Y is absent; or Z is CH₃ and, Y is O; where R⁴ is alkyl, CF₃ or aryl; T is H or OR⁶, where R⁶ is H, alkyl, aryl, COR⁷, P(O)(OR⁸)₂, or SO₃R⁸, where R⁷ and R⁸ are independently selected in each instance from H, alkyl, alkenyl, cycloalkyl, heterocyclyl, aryl, and arylalkyl, each of which is optionally substituted, or R⁸ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (1c) is treated with a compound of formula R²³C(O)CH₂Rᵃ to give a compound of the following formula:

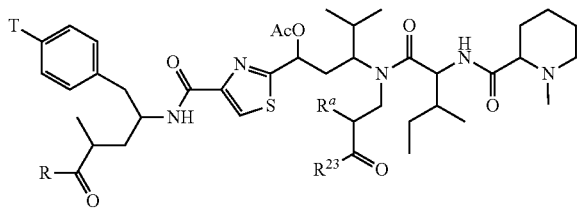

wherein R²³ is H, alkyl, alkenyl, cycloalkyl, aryl, or arylalkyl, each of which is optionally substituted; Rᵃ is C(O)R⁹, C(O)OR⁹ or CN; R⁹ is selected from the group consisting of H, alkyl, alkenyl, cycloalkyl, aryl, and arylalkyl, each of which is optionally substituted: and T is H or OH, or the corresponding carboxylic acid derivative thereof, where R is other than OH.

It is to be understood that the corresponding compounds of formula (2a) may be similarly prepared via the corresponding intermediate of formula (1a) and R²³C(O)CH₂Rᵃ.

In another embodiment, intermediate compound of formula (1b) is treated with water to give a second intermediate compound of the following formula (3b)

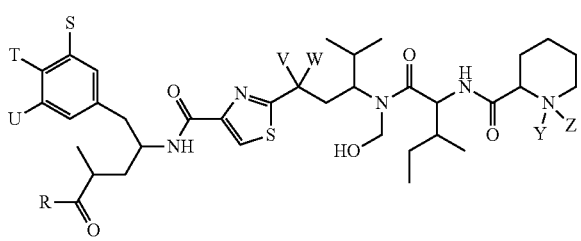

wherein V is H, OR², or halo, and W is H, OR², or alkyl, where R² is independently selected in each instance from H, alkyl, or COR³, where R³ is alkyl, alkenyl, cycloalkyl, aryl or arylalkyl, each of which is optionally substituted, providing that R² is not H when both V and W are OR²; or V and W are taken together with the attached carbon to form a carbonyl; Z is CH₃ or COR⁴, and Y is absent; or Z is CH₃ and, Y is O; where R⁴ is alkyl, CF₃ or aryl; T is H or OR⁶, where R⁶ is H, alkyl, aryl, COR⁷, P(O)(OR⁸)₂, or SO₃R⁸, where R⁷ and R⁸ are independently selected in each instance from H, alkyl, alkenyl, cycloalkyl, heterocyclyl, aryl, and arylalkyl, each of which is optionally substituted, or R⁸ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (1c) is treated with water to give a second intermediate compound of formula (3c):

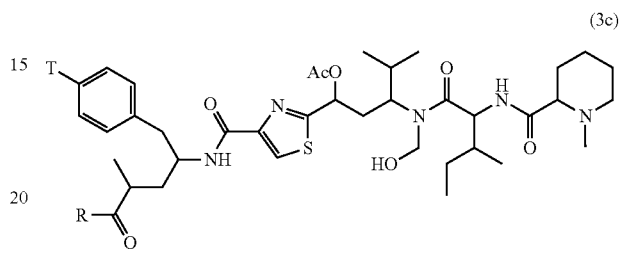

wherein T is H or OH, or the corresponding carboxylic acid derivative thereof, where R is other than OH.

It is to be understood that the corresponding compounds of formula (3a) may be similarly prepared via the corresponding intermediate of formula (1a) and water.

In another embodiment, intermediate compound of formula (3b) is treated with a halogenating, sulfonylating, phosphonylating or phosphorylation reagent to give a compound of the following formula:

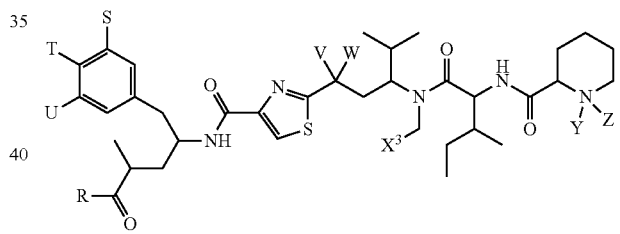

wherein X³ is halogen, OS(O)₂R²⁴, OP(O)(OR²⁴)R²⁴, or OP(O)(OR²⁴)₂; where R²⁴ is independently selected in each instance from the group consisting of H, alkyl, alkenyl, cycloalkyl, aryl, and arylalkyl, each of which is optionally substituted, or R²⁴ is a metal cation; V is H, OR², or halo, and W is H, OR², or alkyl, where R² is independently selected in each instance from H, alkyl, or COR³, where R³ is alkyl, alkenyl, cycloalkyl, aryl or arylalkyl, each of which is optionally substituted, providing that R² is not H when both V and W are OR²; or V and W are taken together with the attached carbon to form a carbonyl; Z is CH₃ or COR⁴, and Y is absent; or Z is CH₃ and, Y is O; where R⁴ is alkyl, CF₃ or aryl; T is H or OR⁶, where R⁶ is H, alkyl, aryl, COR⁷, P(O)(OR⁸)₂, or SO₃R⁸, where R⁷ and R⁸ are independently selected in each instance from H, alkyl, alkenyl, cycloalkyl, heterocyclyl, aryl, and arylalkyl, each of which is optionally substituted, or R⁸ is a metal cation; and S and U are each independently selected from the group consisting of H, halo, nitro, cyano, alkyl, haloalkyl, alkoxy, and haloalkoxy, or the corresponding carboxylic acid derivative thereof, where R is other than OH.

In another embodiment, intermediate compound of formula (3c) is treated with a halogenating, sulfonylating, phosphonylating or phosphorylation reagent to give a compound of the following formula:

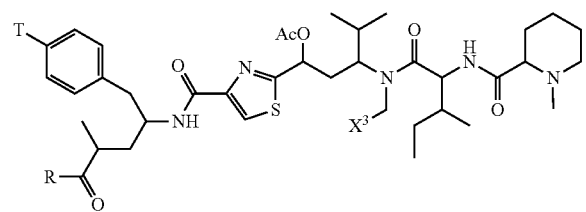

wherein $X^3$ is halogen, $OS(O)_2R^{24}$, $OP(O)(OR^{24})R^{24}$, or $OP(O)(OR^{24})_2$; where $R^{24}$ is independently selected in each instance from the group consisting of H, alkyl, alkenyl, cycloalkyl, aryl, and arylalkyl, each of which is optionally substituted, or $R^{24}$ is a metal cation; and T is H or OH, or the corresponding carboxylic acid derivative thereof, where R is other than OH.

It is to be understood that the corresponding compounds of formula (3a) may be similarly prepared via the corresponding intermediate of formula (1a) and treatment with a halogenating, sulfonylating, phosphonylating or phosphorylation reagent.

In another embodiment, a compound of the following formula (2d):

(2d)

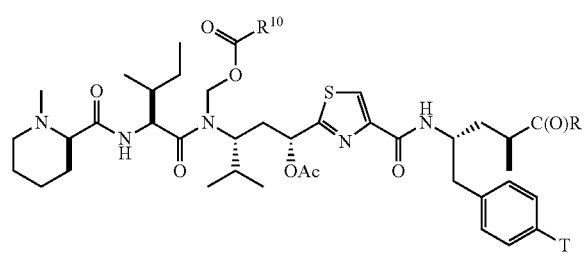

is described, wherein $R^{10}$ is H, alkyl, cycloalkyl, alkenyl, aryl or arylalkyl, each of which is optionally substituted: and T is H or OH, or the corresponding carboxylic acid derivative thereof, where R is other than OH; is treated with trifluoroacetic acid and the mixture is concentrated under reduced pressure to give an intermediate iminium compound. It is understood that such iminium compounds may be present as the corresponding trifluoroacetate salt compounds, and other hydrates and solvates, and as the acylaminal compound, and other addition adducts, as is illustrated by the following formulae:

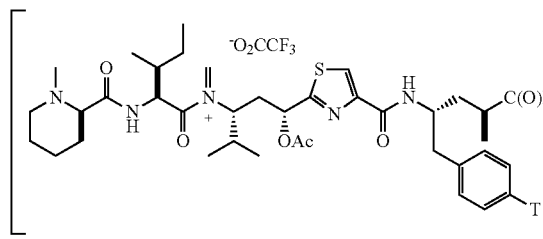

Mixing the compound of those formulae, or other corresponding intermediates described herein and prepared by treatment of compound (2d) with TFA, and with an alcohol gives the corresponding N,O-acetal compound of the following formula:

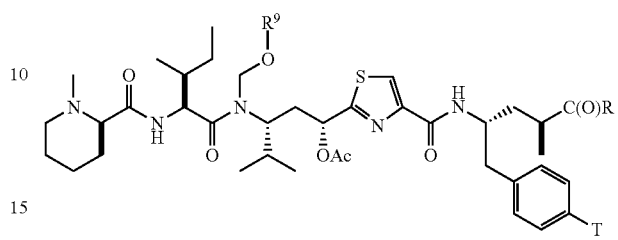

wherein $R^9$ is H, alkyl, alkenyl, cycloalkyl, aryl, or arylalkyl, each of which is optionally substituted, or $R^9$ is $C(O)R^{20}$, $S(O)_2R^{20}$, or $P(O)(OR^{20})_2$; where $R^{20}$ is independently selected in each instance from the group consisting of H, alkyl, alkenyl, cycloalkyl, aryl, and arylalkyl, each of which is optionally substituted, or $R^{20}$ is a metal cation: and T is H or OH, or the corresponding carboxylic acid derivative thereof, where R is other than OH.

In another embodiment, mixing a compound of formula (2d) with trifluoroacetic acid and concentrating the mixture under reduced pressure, followed by mixing the concentrated mixture with a thiol gives a N,S-acetal compound of the following formula:

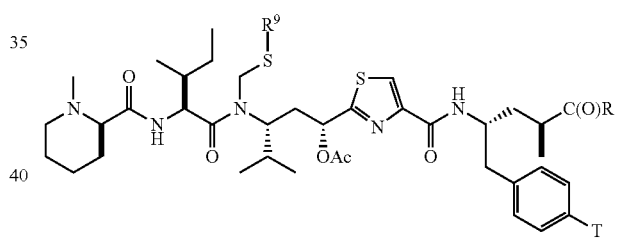

wherein $R^9$ is H, alkyl, alkenyl, cycloalkyl, aryl, or arylalkyl, each of which is optionally substituted, or $R^9$ is $C(O)R^{20}$, $S(O)_2R^{20}$, or $P(O)(OR^{20})_2$; where $R^{20}$ is independently selected in each instance from the group consisting of H, alkyl, alkenyl, cycloalkyl, aryl, and arylalkyl, each of which is optionally substituted, or $R^{20}$ is a metal cation: and T is H or OH, or the corresponding carboxylic acid derivative thereof, where R is other than OH.

In another embodiment, mixing a compound of formula (2d) with trifluoroacetic acid and concentrating the mixture

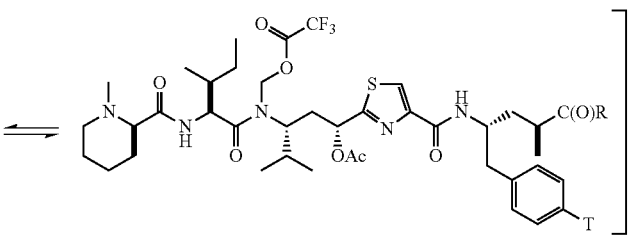

under reduced pressure, followed by mixing the concentrated mixture with a nitrile gives a compound of the following formula:

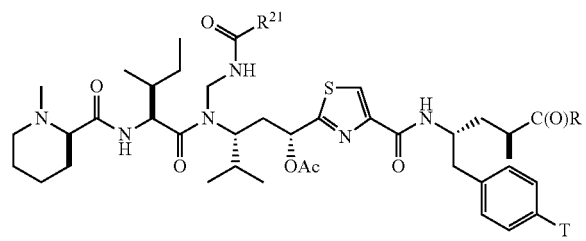

wherein $R^{21}$ is alkyl, alkenyl, cycloalkyl, aryl, or arylalkyl, each of which is optionally substituted; and T is H or OH, or the corresponding carboxylic acid derivative thereof, where R is other than OH.

In another embodiment, mixing a compound of formula (2d) with trifluoroacetic acid and concentrating the mixture under reduced pressure, followed by mixing the concentrated mixture with a ketone, in a Biginelli-type reaction, gives a compound of the following formula:

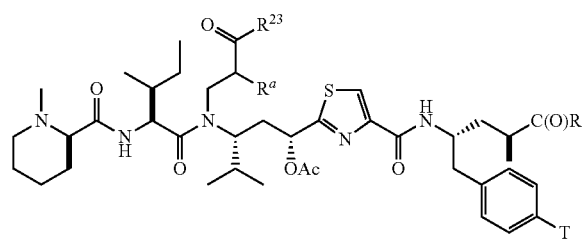

wherein $R^{23}$ is H, alkyl, alkenyl, cycloalkyl, aryl, or arylalkyl, each of which is optionally substituted; $R^a$ is $C(O)R^8$, $C(O)OR^8$ or CN; $R^8$ is selected from the group consisting of H, alkyl, alkenyl, cycloalkyl, aryl, and arylalkyl, each of which is optionally substituted; and T is H or OH, or the corresponding carboxylic acid derivative thereof, where R is other than OH.

In another embodiment, mixing a compound of formula (2d) with trifluoroacetic acid and concentrating the mixture under reduced pressure, followed by mixing the concentrated mixture with an alkenylsilane gives a compound of the following formula:

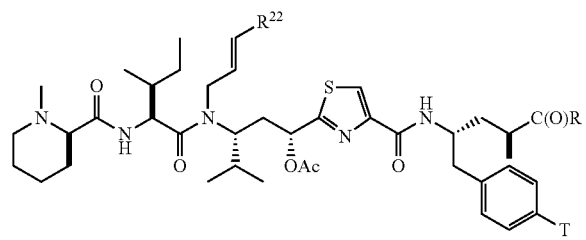

wherein $R^{22}$ is alkyl, alkenyl, cycloalkyl, aryl, or arylalkyl, each of which is optionally substituted; and T is H or OH, or the corresponding carboxylic acid derivative thereof, where R is other than OH.

In another embodiment, mixing a compound of formula (2d) with trifluoroacetic acid and concentrating the mixture under reduced pressure, followed by mixing the concentrated mixture with water gives a compound of formula (3d):

(3d)

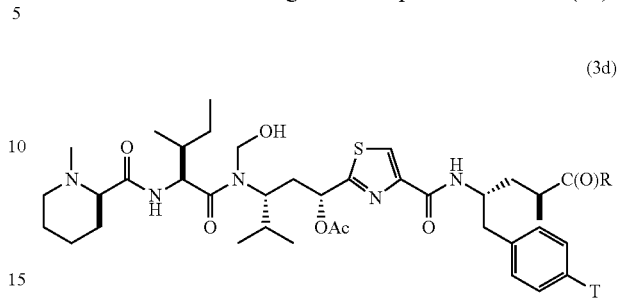

which may also be referred to as hydroxytubulysin D when T is OH, or hydroxytubulysin A when T is OH, or the corresponding carboxylic acid derivative thereof, where R is other than OH.

In another embodiment, N-hydroxymethytubulysin A or N-hydroxymethytubulysin D is treated with a sulfonyl halide and a base to give a compound of the following formula:

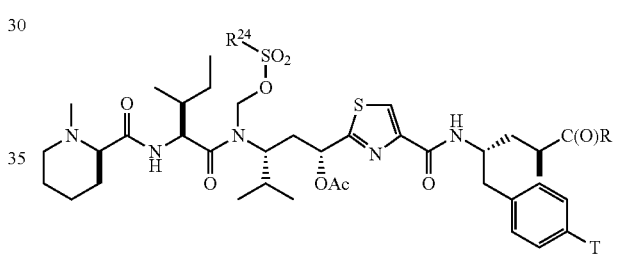

wherein $R^{24}$ is alkyl, cycloalkyl, alkenyl, aryl or arylalkyl, each of which is optionally substituted; and T is H or OH, or the corresponding carboxylic acid derivative thereof, where R is other than OH.

In another embodiment, N-hydroxymethytubulysin A or N-hydroxymethytubulysin D is treated with a bromine or iodine in the presence of triphenylphospine and imidazole to give a compound of the following formula:

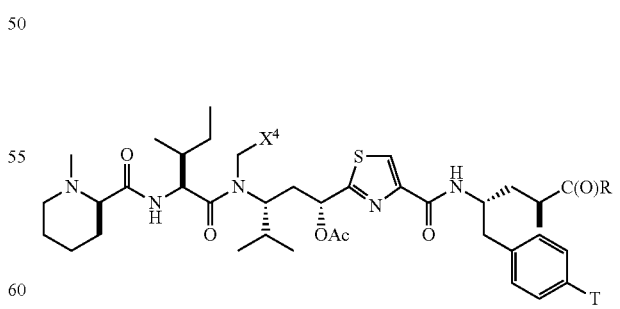

wherein $X^4$ is Br or I; and T is H or OH, or the corresponding carboxylic acid derivative thereof, where R is other than OH.

In another embodiment, conjugates of tubulysins of the following formula are described:

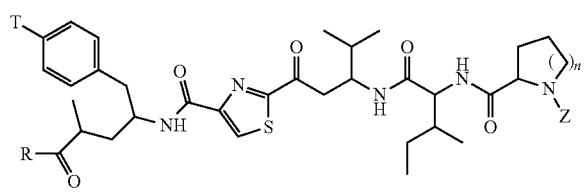

and pharmaceutical salts thereof, where n is 1-3; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation, or $R^6$ is a phenol protecting group, or a prodrug moiety; Z is alkyl or $C(O)R^4$, where $R^4$ is alkyl, $CF_3$, or aryl; and R is OH or a leaving group, or R forms a carboxylic acid derivative. Illustrative examples of such compounds, and their preparation are described in J. Med. Chem. 51, 1530-1533 (2008), the disclosure of which is incorporated herein by reference. It is understood that the conjugates may be formed at any heteroatom in the foregoing formula by removing the corresponding hydrogen or other group, including but not limited to conjugates formed by removing the hydrogen from R when R=OH, from T when T=OH, and the like. Conjugates described herein may include spacer linkers and/or releasable linkers as generally described in US Patent Application Publication 2005/0002942, the disclosure of which is incorporated herein by reference. In addition, conjugates described herein may include targeting ligands, including but not limited to folate and analogs and derivatives of folate, for targeting the conjugates to pathogenic cell populations, such as generally described in US Patent Application Publication 2005/0002942.

In another embodiment, tubulysins of the following general formula are described

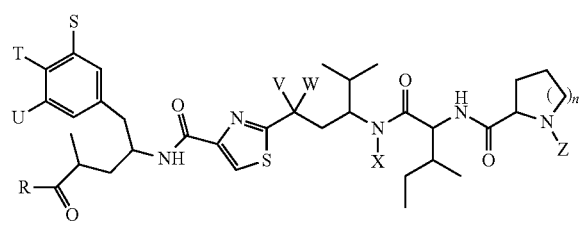

and pharmaceutical salts thereof, where n is 1-3;

V is H, $OR^2$, or halo, and W is H, $OR^2$, or alkyl, where $R^2$ is independently selected in each instance from H, alkyl, or $COR^3$, where $R^3$ is alkyl, alkenyl or aryl, providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl;

Z is $CH_3$ or $COR^4$, and Y is absent; or Z is $CH_3$ and, Y is O; where $R^4$ is alkyl, $CF_3$ or aryl;

T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation;

S and U are each independently selected from the group consisting of H, halo, nitro, cyano, alkyl, haloalkyl, alkoxy, and haloalkoxy; and R is OH or a leaving group, or R forms a carboxylic acid derivative. Additional tubulysins are described in US patent application publication Nos. 2006/0128754 and 2005/0239713, the disclosures of which are incorporated herein by reference.

In another embodiment, tubulysins of the following formula are described:

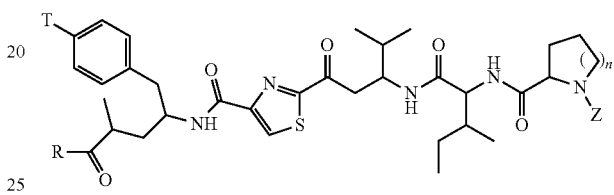

and pharmaceutical salts thereof, where n is 1-3; T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation, or $R^6$ is a phenol protecting group, or a prodrug moiety; Z is alkyl or $C(O)R^4$, where $R^4$ is alkyl, $CF_3$, or aryl; and R is OH or a leaving group, or R forms a carboxylic acid derivative. Illustrative examples of such compounds, and their preparation are described in J. Med. Chem. 51, 1530-1533 (2008), the disclosure of which is incorporated herein by reference.

In another embodiment, tubulysins of the following formula are described:

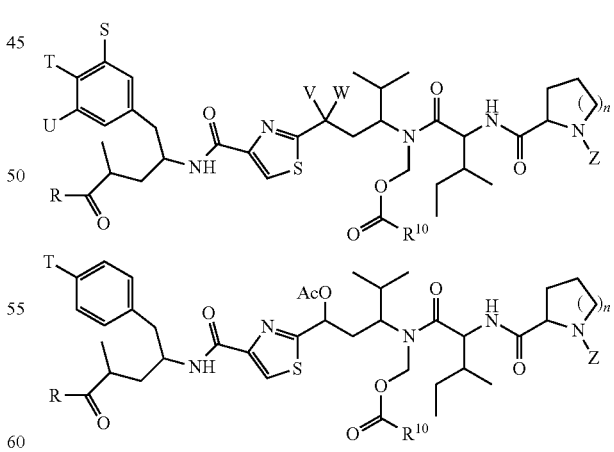

and pharmaceutical salts thereof, where n, S, T, U, V, W, Z, R, and $R^{10}$ are as described in the various embodiments herein.

In another embodiment, tubulysins of the following formula are described:

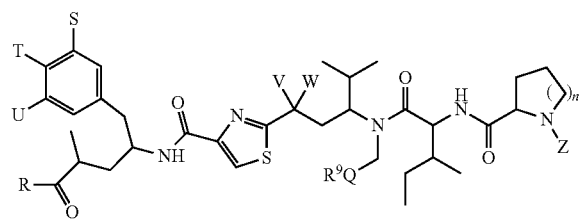

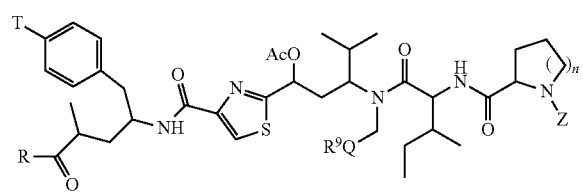

and pharmaceutical salts thereof, where n, S, T, U, V, W, Z, QR⁹, and R are as described in the various embodiments herein. In one variation, Q is —N—, —O—, or —S—; and R⁹ is H, alkyl, alkenyl, cycloalkyl, aryl, or arylalkyl, each of which is optionally substituted. In another variation, QR⁹ are taken together to form $C(O)R^{10}$, $S(O)_2R^{10}$, $P(O)(OR^{10a})_2$, where $R^{10}$ and $OR^{10a}$ are independently selected in each instance from the group consisting of H, alkyl, alkenyl, cycloalkyl, aryl, and arylalkyl, each of which is optionally substituted, or $R^{10a}$ is a metal cation.

In another embodiment, tubulysins of the following formula are described:

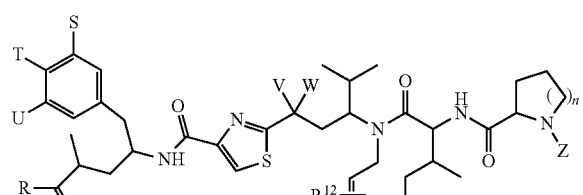

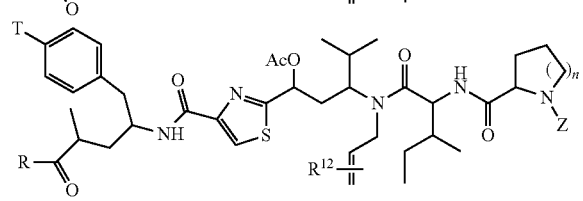

and pharmaceutical salts thereof, where $R^{12}$ represents 1 or more substituents selected from alkyl, alkenyl, cycloalkyl, aryl, and arylalkyl, each of which is optionally substituted; and where n, S, T, U, V, W, Z, and R are as described in the various embodiments herein. It is to be understood that other olefins may form by isomerization, depending on the conditions of the reaction and the identity of $R^1$. For example, when $R^1$ is alkyl, it is appreciated that under the reaction conditions, the double bond can migrate to other carbon atoms along the alkenyl chain, including to form the terminal or wω-olefin.

In another embodiment, tubulysins of the following formula are described:

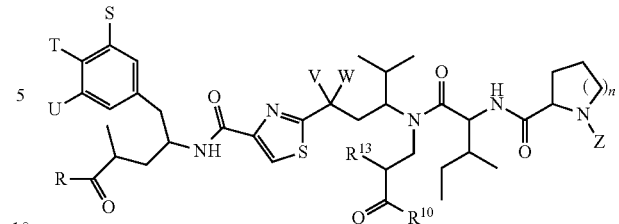

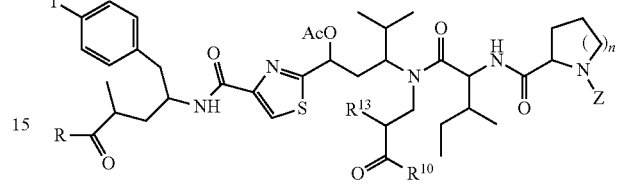

and pharmaceutical salts thereof, where $R^{13}$ is $C(O)R^{10}$, $C(O)OR^{10}$ or CN; and where n, S, T, U, V, W, Z, R, and $R^{10}$ are as described in the various embodiments herein, where $R^{10}$ is independently selected in each instance.

In another embodiment, tubulysins of the following formula are described:

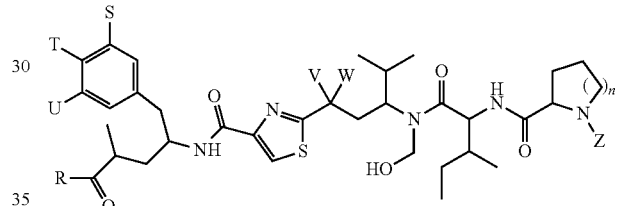

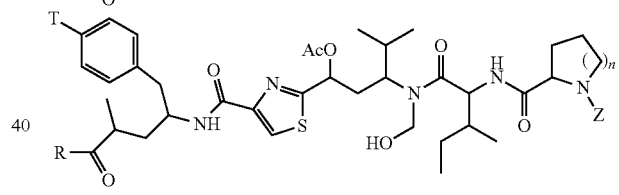

and pharmaceutical salts thereof, where n, S, T, U, V, W, Z, and R are as described in the various embodiments herein.

In another embodiment, tubulysins of the following formula are described:

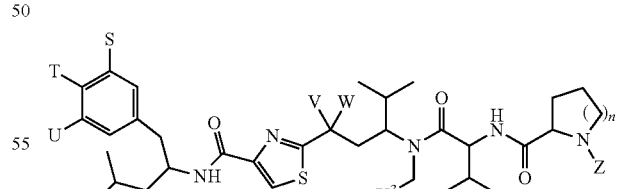

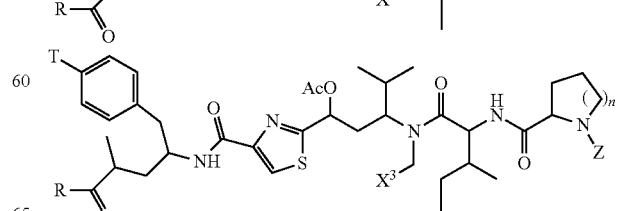

and pharmaceutical salts thereof, where $X^3$ is halogen, $OS(O)_2R^{10}$, $OP(O)(OR^{10a})R^{10}$, or $OP(O)(OR^{10a})_2$; where $R^{10}$ and $R^{10a}$ are independently selected in each instance from the group consisting of H, alkyl, alkenyl, cycloalkyl, aryl, and arylalkyl, each of which is optionally substituted, or $R^{10a}$ is a metal cation; and where n, S, T, U, V, W, Z, and R are as described in the various embodiments herein.

Additional tubulysins useful in preparing the conjugates described herein are described in Peltier et al., "The Total Synthesis of Tubulysin D," J. Am. Chem. Soc. 128:16018-19 (2006), the disclosure of which is incorporated herein by reference.

In each of the foregoing embodiments, it is understood that in one variation, the compounds of the various formulae have the following absolute configuration:

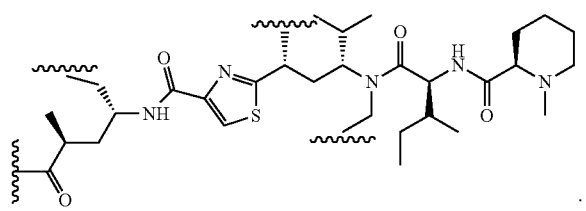

at the indicated asymmetric backbone carbon atoms.

As described herein, the tubulysin compounds may be inhibitors of tubulin polymerization, and also may be DNA-alkylators. Accordingly, methods for treating diseases and disease states including pathogenic cell populations, such as cancer, are described herein.

EXAMPLES

General Procedures

Trifluoroacetic acid (TFA, 0.20 mL) was added via syringe into a light brown solution of a tubulysin mixture (20 mg, containing tubulysins A, B, C, G, I and hydroxytubulysin) in anhydrous dichloromethane (DCM, 0.80 mL). After stirring for 40 minutes at room temperature and under argon, to the solution was added the correspondending nucleophile (for example, but not limited to, $H_2O$, MeOH, 1-propanol, ethylene glycol, 3-methylbutanol, 1-propanethiol, 2-sulfanylethanol, 1,2-ethanedithiol, acetic acid, butyric acid, trans-4-chloro-2-butenoic acid), 0.20 mL was used for all thiols and 0.50 mL was used for all the others, and the solution was concentrated at reduced pressure on a Büchi Rotavapor and then further concentrated by means of an oil pump. The crude product was dissolved in dimethyl sulfoxide (DMSO, 1.0 mL) and purified by preparative HPLC to afford the product as a white solid.

GENERAL PREPARATIVE HPLC PARAMETERS

Column: Waters XTerra Prep MS C18 10 µm, 19×250 mm; Mobile phase A: 2.0 mM sodium phosphate buffer, pH 7.0; Mobile phase B: acetonitrile; Method: 10% B to 80% B over 30 minutes, flow rate=26 mL/min.

Example

Interconversion of natural tubulysins

TFA (1.0 mL) was added to a light brown solution of a mixture of tubulysins (105 mg tubulysins A, B, C, G, I and hydroxy-tubulysin A) in dry DCM (5.0 mL) and the resulting light brown-greenish solution was stirred at room temperature under argon for 50 minutes. LC/MS indicated that the tubulysin mixture was converted to hydroxy-tubulysin. To the solution was added butyric acid (10 mL) and the solution was first concentrated by evaporation to a small volume to remove TFA and DCM, and then further concentrated to a thick oil under vacuum over about 1 hour. HPLC analysis indicated a complete conversion of the hydroxy tubulysin intermediate to tubulysin B. The crude product was dissolved in DMSO (1.2 mL) and purified by preparative HPLC on a Waters XTerra Prep MS $C_{18}$ 10 µm 19×250 mm column using a 25% B to 50% B gradient over 20 minutes (A: 2.0 mM phosphate buffer, pH 7.0; B: ACN) at 25 mL/minute. Fractions from 11.5 to 13.5 minutes were collected and lyophilized to 86 mg of a white solid containing 77 mg of tubulysin B and 9.0 mg of sodium phosphate salts. Monitoring the interconversion throughout the experiment by HPLC showed conversion only to tubulysin B, as compared to a reference standard sample. It is to be understood that other mixtures of tubulysins can be similarly converted into a single tubulysin. It is further to be understood that this and other mixtures of tubulysins can be similarly converted into a different tubulysin than tubulysin B.

Example

Interconversion of natural tubulysins

The conditions of the previous Example were repeated to (a) convert tubulysin A into tubulysin B, (b) convert tubulysin A into tubulysin I, (c) convert a mixture of tubulysins A and B into tubulysin B, and (d) convert a mixture of tubulysins A, B, and I into tubulysin B. In each case, the yield of tubulysin B was ≥90%. It is to be understood that in each of examples (a) to (d), the corresponding tubulysin can be converted into a different tubulysin than tubulysin B. It is further to be understood that tubulysin B can be similarly converted into a different tubulysin. In some cases, N-hydroxymethyl substituted tubulysin was also isolated. It was surprisingly discovered that this hemiaminal was stable at neutral pH, and did not decompose to the free amine and formaldehyde.

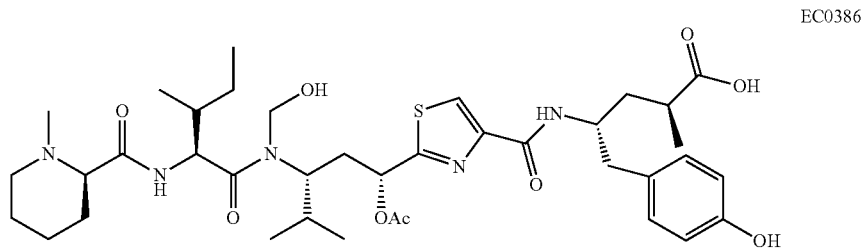 [SMILES: CCC(C)[C@H](NC(=O)[C@H]1CCCCN1C)C(=O)N(CO)[C@H](C[C@@H](OC(C)=O)c1nc(C(=O)N[C@@H](Cc2ccc(O)cc2)C[C@H](C)C(=O)O)cs1)C(C)C]

The ¹H NMR spectrum of hydroxytubulysin A was consistent with the structure; the MS had an m/z=760. The ¹H NMR spectrum of tubulysin B obtained in this experiment was consistent with the structure; the MS had an m/z=830.

Example

Methoxy Tubulysin (EC0313)

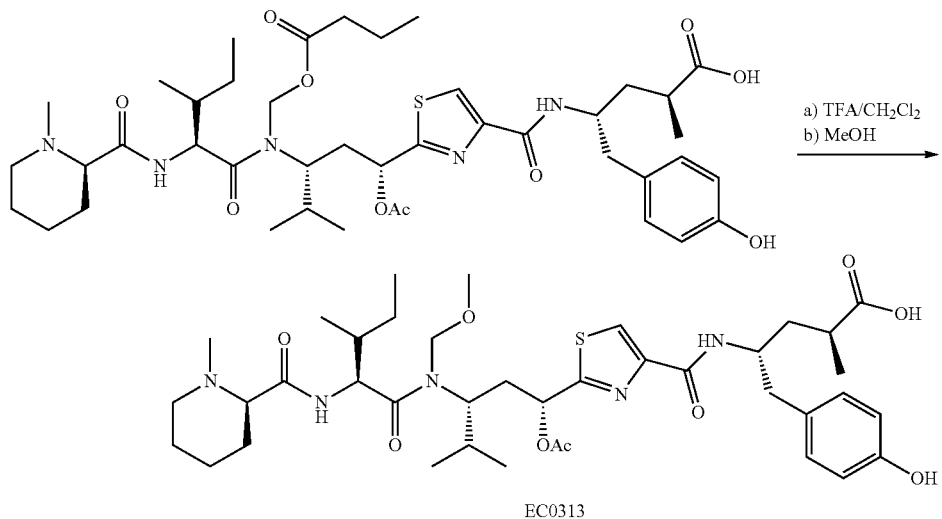

TFA (0.20 mL) was added to a solution of tubulysin B (21.0 mg) in dry DCM (0.80 mL) and the mixture was stirred at room temperature under argon for 1 hour. MeOH (1.0 mL) was added to the stirring solution and the solvent was evaporated after 1 h. The residue was purified by preparative HPLC on a Waters XTerra Prep MS C$_{18}$ 10 μm 19×250 mm column using a 20% B to 50% B gradient over 25 minutes (A: 1.0 mM phosphate buffer, pH 7.0; B: ACN) at 10 mL/minute. Fractions from 18.8 to 22.3 minutes were collected and lyophilized to 18.0 mg of a white solid containing 15.5 mg of title compound and 2.5 mg of sodium phosphate salts. The ¹H NMR spectrum of methoxy tubulysin obtained in this experiment was consistent with the structure; the MS had an m/z=774.

Example

2-Hydroxyethoxy Tubulysin (EC0346)

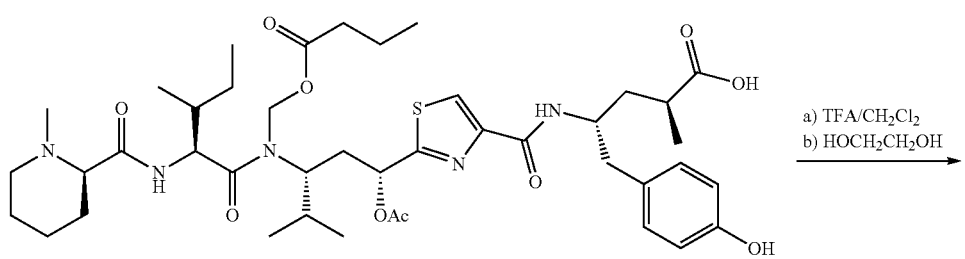

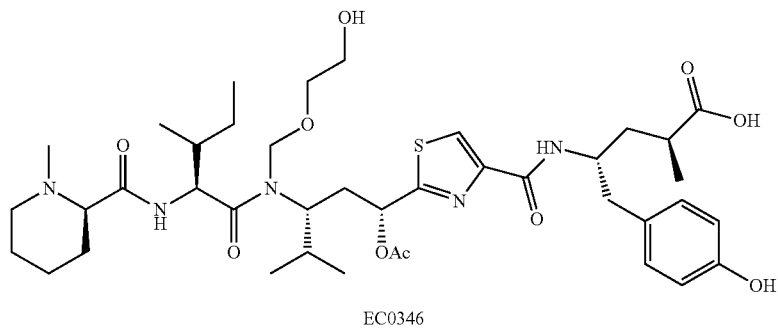

EC0346

TFA (75 μL) was added to a solution of tubulysin B (4.8 mg) in dry DCM (0.30 mL) and the mixture was stirred at room temperature under argon for 1 hour. Ethylene glycol (0.30 mL) was added to the stirring solution and the solvent was evaporated after 30 min. The residue was purified by a preparative HPLC on a Waters Phenomenex Luna $C_{18}$ 10 μm 4.6×250 mm column using a 10% B to 80% B gradient over 20 minutes (A: 1.0 mM phosphate buffer, pH 7.0; B: ACN) at 2.5 mL/minute. Fractions from 6.3 to 6.7 minutes were collected and lyophilized to 4.9 mg of a white solid containing 4.8 mg of title compound and 0.1 mg of sodium phosphate salts. The $^1$H NMR spectrum of 2-hydroxyethoxy tubulysin obtained in this experiment was consistent with the structure; the MS had an m/z=804.

Example

2-Mercaptoethylthio Tubulysin (EC0374)

TFA (60 μL) was added to a solution of tubulysin B (6.9 mg) in dry DCM (0.54 mL) and the mixture was stirred at room temperature under argon for 30 minutes. 1,2-Ethanedithiol (2.0 μL) was added to the stirring solution and the solvent was evaporated after 5 h. The residue was purified by preparative HPLC on a Waters XTerra Prep MS $C_{18}$ 10 μm 19×250 mm column using a 10% B to 80% B gradient over 20 minutes (A: 2.0 mM phosphate buffer, pH 7.0; B: ACN) at 25 mL/minute. Fractions from 9.5 to 10.7 minutes were collected and lyophilized to 7.7 mg of a white solid containing 3.4 mg of title compound and 4.3 mg of sodium phosphate salts. The $^1$H NMR spectrum of 2-mercaptoethylthio tubulysin obtained in this experiment was consistent with the structure; the MS had an m/z=836.

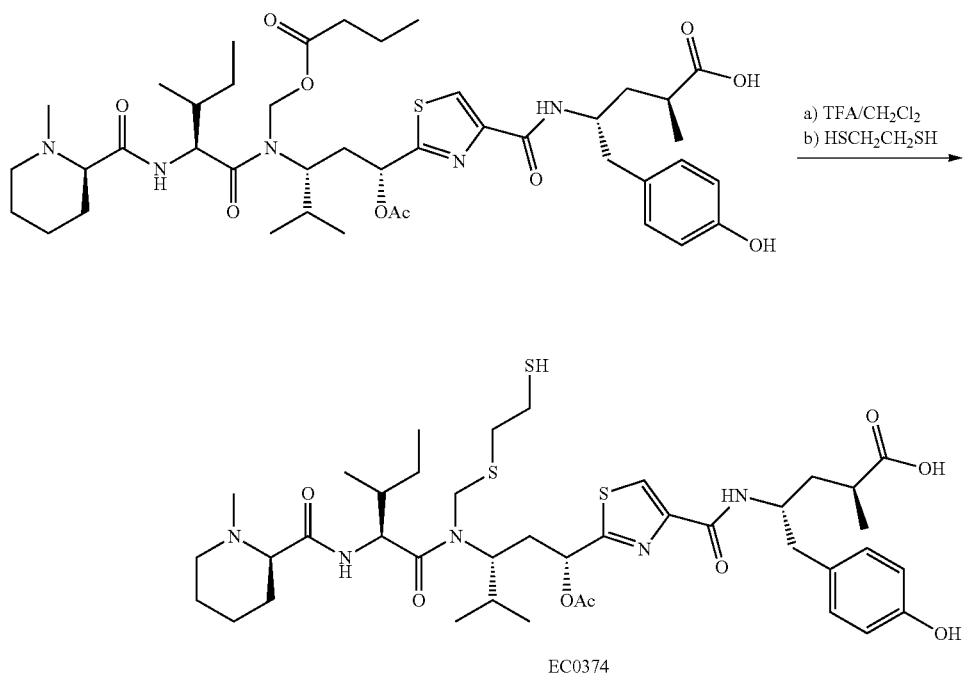

EC0374

Example iso-Butyrylamidotubulysin (EC0585)

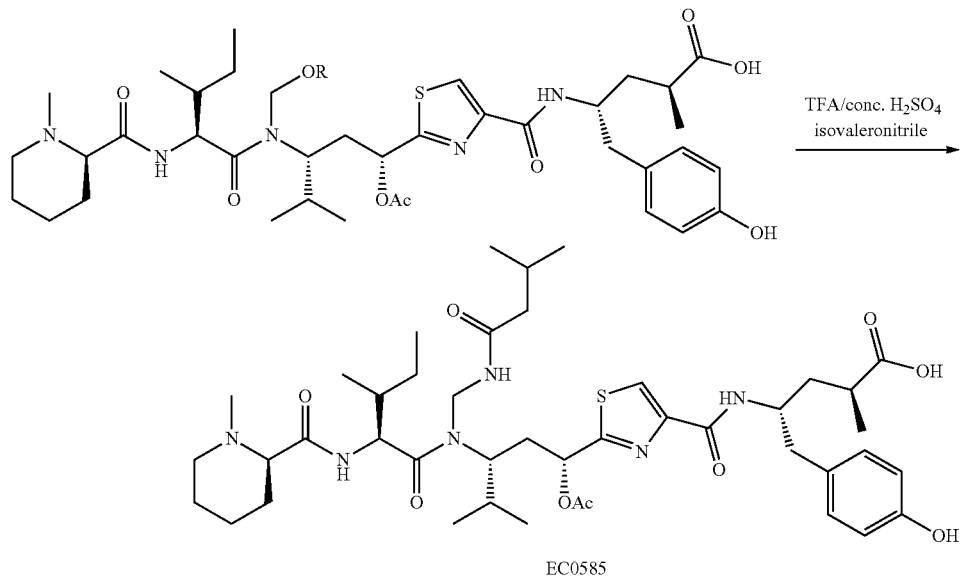

A mixture of tubulysins containing factors A, B, C, G, I, and hydroxy tubulysin (R=C(O)CH$_2$CH(CH$_3$)$_2$, C(O)CH$_2$CH$_2$CH$_3$, C(O)CH$_2$CH$_3$, C(O)CH=C(CH$_3$)$_2$, C(O)CH$_3$, and H, respectively) was converted to a single tubulysin. To a solution of the tubulysin mixture (25 mg) in isovaleronitrile (150 μL) was added a solution containing TFA (30 μL), concentrated H$_2$SO$_4$ (20 μL), and isovaleronitrile (150 μL). After stirring at room temperature for 22 hours, the reaction was quenched with 2.0 mM sodium phosphate buffer (pH=7.0, 15 mL) and injected into a preparative HPLC for purification. Column: Waters XTerra Prep MS C$_{18}$ 10 μm, 19×250 mm; Mobile phase A: 2.0 mM sodium phosphate buffer, pH 7.0; Mobile phase B: acetonitrile; Method: 10% B to 80% B over 30 minutes, flow rate=26 mL/min. Fractions from 17.22-18.36 minutes were collected and lyophilized to produce EC0585 as a white solid (16 mg). The $^1$H NMR spectrum of iso-butyrylamidotubulysin obtained in this experiment was consistent with the structure; the MS had an m/z=843.

Example

N-Homoallyl Tubulysin EC0550

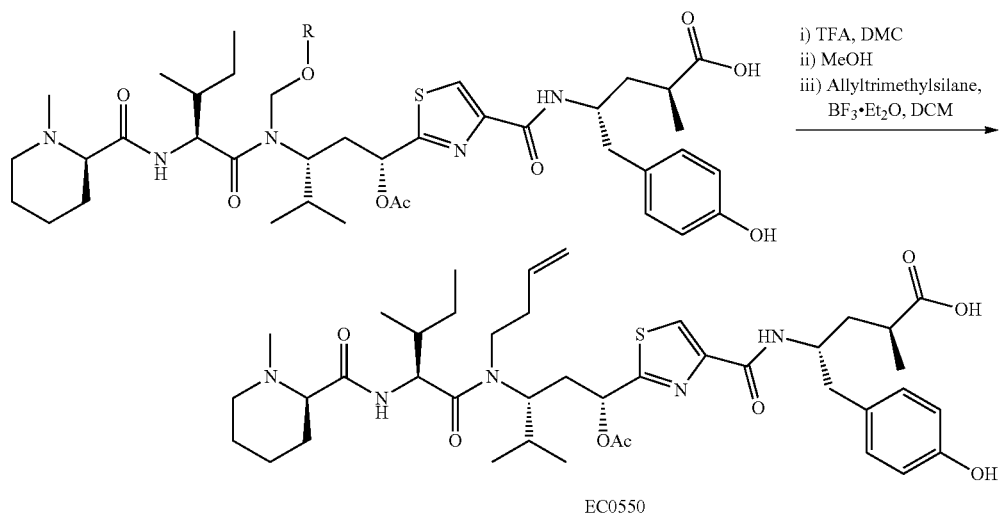

A mixture of tubulysins containing factors A, B, C, G, I, and hydroxy tubulysin (R=C(O)CH$_2$CH(CH$_3$)$_2$, C(O)CH$_2$CH$_2$CH$_3$, C(O)CH$_2$CH$_3$, C(O)CH=C(CH$_3$)$_2$, C(O)CH$_3$, and H, respectively) was converted to a single tubulysin. TFA (0.15 mL) was added to a solution of the tubulysin mixture (19 mg) in anhydrous DCM (0.60 mL) at room temperature. After stirring for 40 minutes at room temperature under argon, the reaction was quenched with anhydrous MeOH (0.50 mL). The solution was concentrated on a Büchi Rotavapor, co-evaporated with anhydrous MeOH (2×) and anhydrous DCM (2×), vacuumed for 30 minutes, co-evaporated again with anhydrous MeOH and anhydrous DCM (2×), and vacuumed for an additional 1.5 hours. The residue was dissolved in anhydrous DCM (0.75 mL), to which was added allyltrimethylsilane (0.30 mL), cooled in an ice-bath, and to which was added $BF_3.Et_2O$ (0.23 mL). The reaction mixture was stirred under argon in an ice-bath for 30 minutes, and then the cooling was removed and the reaction mixture was stirred at room temperature for an additional 2 hours and 50 minutes. The reaction mixture was concentrated and the residue was purified by a preparative HPLC. Column: Waters XTerra Prep MS $C_{18}$ 10 µm, 19×250 mm; Mobile phase A: 2.0 mM sodium phosphate buffer, pH 7.0; Mobile phase B: acetonitrile; Method: 15% B to 80% B over 30 minutes, flow rate=26 mL/min. Fractions from 14.41-15.17 minutes were collected and lyophilized to afford EC0550 as a white solid (10 mg). The $^1H$ NMR spectrum of N-homoallyl tubulysin obtained in this experiment was consistent with the structure; the MS had an m/z=784.

Example

Synthesis of Tubulysin B Hydrazide EC0347

Prep MS $C_{18}$ 10 µm, 19×250 mm; Mobile phase A: 1.0 mM sodium phosphate buffer, pH 7.0; Mobile phase B: acetonitrile; Method: 10% B to 80% B over 20 minutes, flow rate=25 mL/min. Fractions from 15.14-15.54 minutes were collected and lyophilized to produce EC0347 as a white solid (2.7 mg). The $^1H$ NMR spectrum of tubulysin B hydrazide obtained in this experiment was consistent with the structure; the MS had an m/z=844.

Example

Synthesis of EC0311

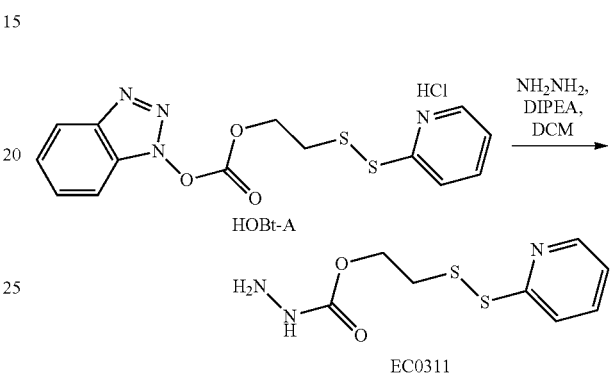

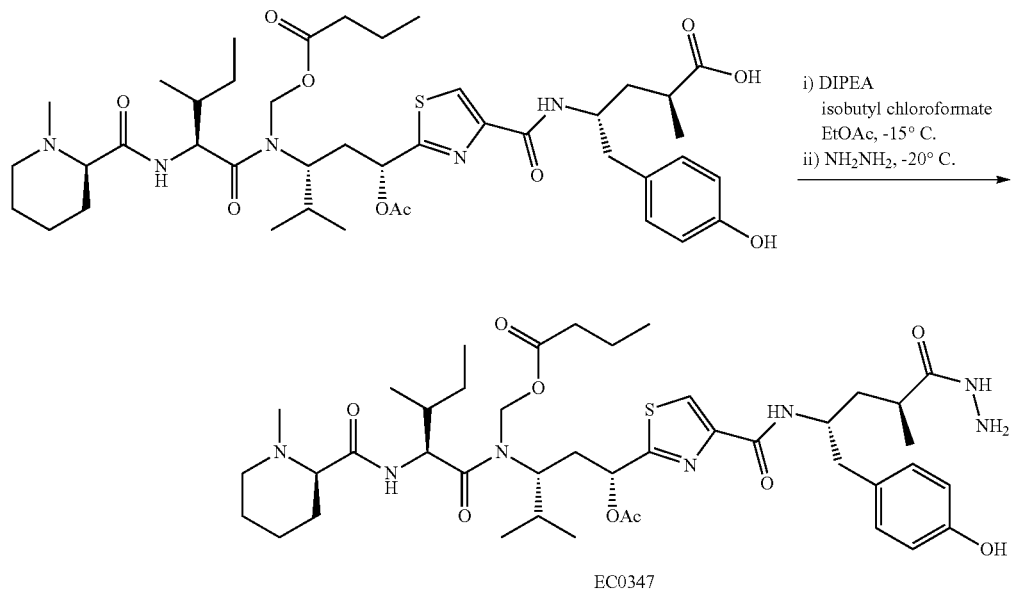 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)O)cs1)C(C)C ; CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NN)cs1)C(C)C]

N,N-Diisopropylethylamine (DIPEA, 6.1 µL) and isobutyl chloroformate (3.0 µL) were added with the help of a syringe in tandem into a solution of tubulysin B (0.15 mg) in anhydrous EtOAc (2.0 mL) at −15° C. After stirring for 45 minutes at −15° C. under argon, the reaction mixture was cooled down to −20° C. and to which was added anhydrous hydrazine (5.0 µL). The reaction mixture was stirred under argon at −20° C. for 3 hours, quenched with 1.0 mM sodium phosphate buffer (pH 7.0, 1.0 mL), and injected into a preparative HPLC for purification. Column: Waters XTerra DIPEA (0.60 mL) was added to a suspension of HOBt-A (685 mg, 91%) in anhydrous DCM (5.0 mL) at 0° C., stirred under argon for 2 minutes, and to which was added anhydrous hydrazine (0.10 mL). The reaction mixture was stirred under argon at 0° C. for 10 minutes and room temperature for an additional 30 minutes, filtered, and the filtrate was purified by flash chromatography (silica gel, 2% MeOH in DCM) to afford EC0311 as a clear thick oil (371 mg), solidified upon standing.

Example

Synthesis of EC0312

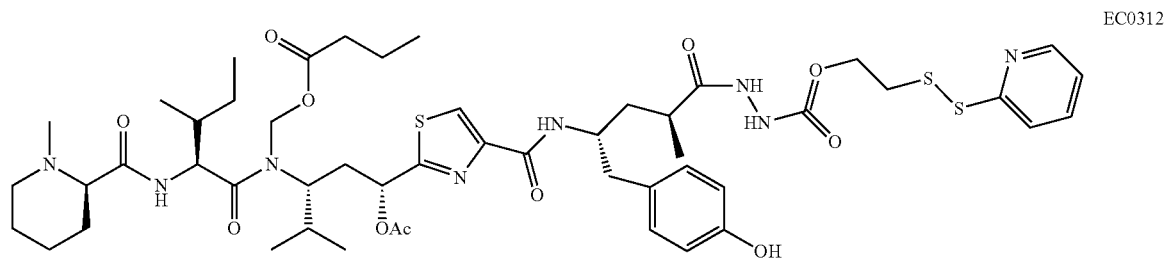

DIPEA (36 µL) and isobutyl chloroformate (13 µL) were added with the help of a syringe in tandem into a solution of tubulysin B (82 mg) in anhydrous EtOAc (2.0 mL) at −15° C. After stirring for 45 minutes at −15° C. under argon, to the reaction mixture was added a solution of EC0311 in anhydrous EtOAc (1.0 mL). The resulting solution was stirred under argon at −15° C. for 15 minutes and room temperature for an additional 45 minutes, concentrated, and the residue was purified by flash chromatography (silica gel, 2 to 8% MeOH in DCM) to give EC0312 as a white solid (98 mg). The $^1$H NMR spectrum of EC0312 obtained in this experiment was consistent with the structure; the MS had an m/z=1057.

Example

The following compounds were prepared according to the procedures described herein.

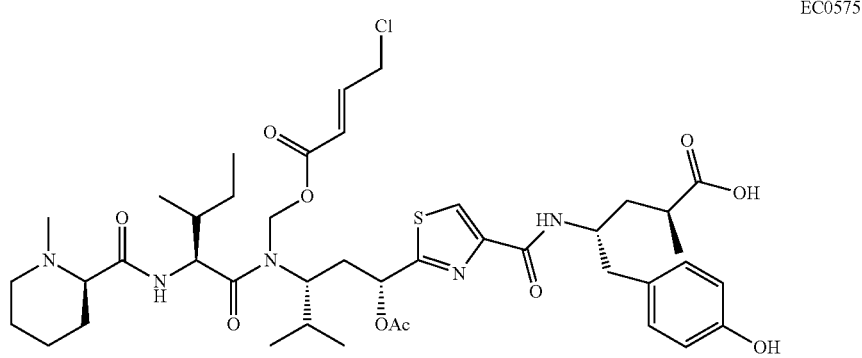 [SMILES: CCC(C)[C@H](NC(=O)[C@H]1CCCCN1C)C(=O)N(COC(=O)/C=C/CCl)[C@H](C[C@@H](OC(C)=O)c1nc(C(=O)N[C@@H](Cc2ccc(O)cc2)C[C@H](C)C(=O)O)cs1)C(C)C]

The $^1$H NMR spectrum of EC0575 obtained in this experiment was consistent with the structure; the MS had an m/z=862.

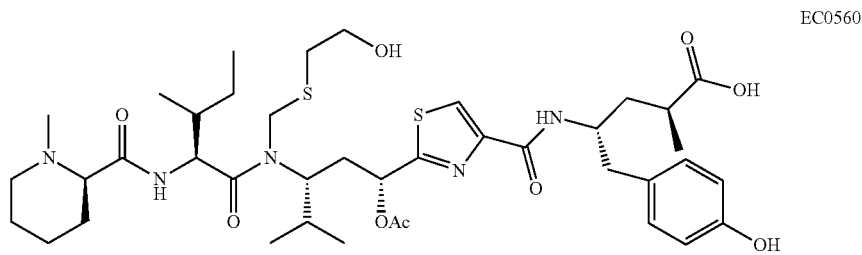 [SMILES: CCC(C)[C@H](NC(=O)[C@H]1CCCCN1C)C(=O)N(CSCCO)[C@H](C[C@@H](OC(C)=O)c1nc(C(=O)N[C@@H](Cc2ccc(O)cc2)C[C@H](C)C(=O)O)cs1)C(C)C]

The ¹H NMR spectrum of EC0560 obtained in this experiment was consistent with the structure; the MS had an m/z=820.

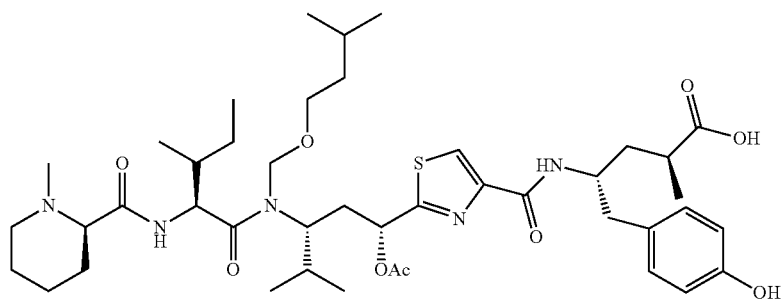

EC0356

The ¹H NMR spectrum of EC0356 obtained in this experiment was consistent with the structure; the MS had an m/z=817.

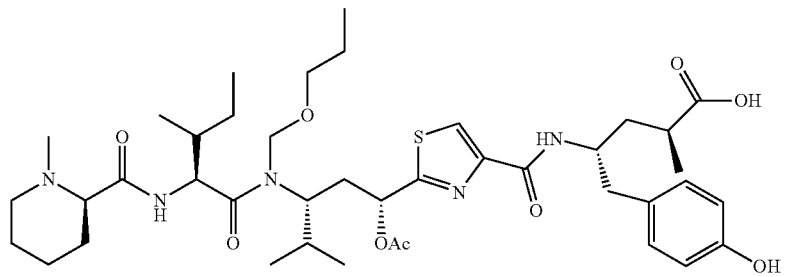

EC0611

The ¹H NMR spectrum of EC0611 obtained in this experiment was consistent with the structure; the MS had an m/z=802.

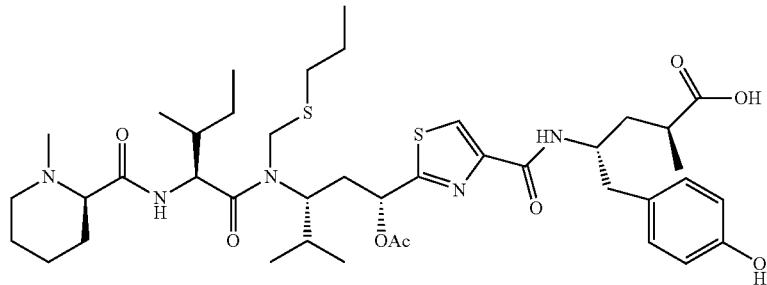

EC0623

The ¹H NMR spectrum of EC0623 obtained in this experiment was consistent with the structure; the MS had an m/z=818.

It is appreciated that the foregoing Examples are merely illustrative of the processes described herein and that many routine modifications may be made to prepare additional tubulysin compounds, and analogs and derivatives thereof. For example, additional ether forming alcohols may be used, including but not limited to alcohols, such as ethanol, propanol, sec-butanol, and the like, polyols, such as ethylene glycols, polyethylene glycols, propylene glycols, polypropylene glycols, glycerol, and the like, including alkyl, and acyl derivatives thereof, aminoalcohols, such as aminoethanol, aminopropanol, polyaminoalkylethanol, and the like, including alkyl, and acyl derivatives thereof, and others.

Similarly, additional thiols, carboxylic acids, amino acids, amines, and the like may be used as nucleophiles to trap the intermediate iminium compounds of formulae (1) and (3).

Method Example

Inhibition of Cellular DNA Synthesis

The compounds described herein are evaluated using an in vitro cytotoxicity assay that predicts the ability of the drug to inhibit the growth of folate receptor-positive KB cells. The KB cells are exposed for up to 7 h at 37° C. over a range of concentrations of folate-drug conjugate in the absence or presence of at least a 100-fold excess of folic acid. The cells are then rinsed once with fresh culture medium and incubated in fresh culture medium for 72 hours at 37° C. Cell viability is assessed using a ³H-thymidine incorporation assay.

Method Example

In vitro concentration-dependent cytotoxic activity

Cells were heavily seeded in 24-well Falcon plates and allowed to form nearly confluent monolayers overnight. Thirty minutes prior to the addition of test article, spent medium was aspirated from all wells and replaced with fresh folate-free RPMI (FFRPMI). Note, designated wells received media containing 100 μM folic acid; and, cells within the latter wells were used to determine the targeting specificity, since cytotoxic activity produced in the presence of excess folic acid (enables competition for FR binding) would signify the portion of the total activity that was unrelated to FR-specific delivery. Following one rinse with 1 mL of fresh FFRPMI containing 10% heat-inactivated fetal calf serum, each well received 1 mL of media containing increasing concentrations of test article (4 wells per sample) in the presence or absence of 100 μM free folic acid (a binding site competitor). Treated cells were pulsed for 2 h at 37° C., rinsed 4 times with 0.5 mL of media, and then chased in 1 mL of fresh media up to 70 h. Spent media was aspirated from all wells and replaced with fresh media containing 5 μCi/mL ³H-thymidine. Following a further 2 h 37° C. incubation, cells were washed 3 times with 0.5 mL of PBS and then treated with 0.5 mL of ice-cold 5% trichloroacetic acid per well. After 15 min, the trichloroacetic acid was aspirated and the cell material solubilized by the addition of 0.5 mL of 0.25 N sodium hydroxide for 15 min. Four hundred and fifty μL of each solubilized sample were transferred to scintillation vials containing 3 mL of Ecolume scintillation cocktail and then counted in a liquid scintillation counter. Final results are expressed as the percentage of ³H-thymidine incorporation relative to untreated controls.

As shown in the following table, dose-dependent cytotoxicity is measurable, and in most cases, the $IC_{50}$ values (concentration of drug conjugate required to reduce ³H-thymidine incorporation into newly synthesized DNA by 50%) are in the low nanomolar range. Furthermore, the cytotoxicities of these conjugates are reduced in the presence of excess free folic acid, indicating that the observed cell killing was mediated by binding to the folate receptor.

| Example | Cytotoxicity $IC_{50}$ (nM) |
| --- | --- |
| Tubulysin A | 2 |
| Tubulysin B | 2.6 |
| EC0313 | 9 |
| EC0346 | 18 |
| EC0550 | 2 |
| EC0356 | 12 |
| EC0374 | 24 |
| EC0585 | 8 |
| EC0386 | 42 |
| EC0623 | 0.48 |
| EC0346 | 18 |

Method Example

Tumor models and therapy

Four to seven week-old mice (Balb/c or nu/nu strains) are purchased from Harlan Sprague Dawley, Inc. (Indianapolis, Ind.). Since normal rodent chow contains a high concentration of folic acid (6 mg/kg chow), mice used in these studies are maintained on the folate-free diet (Harlan diet #TD00434) for 1 week before tumor implantation to achieve serum folate concentrations close to the range of normal human serum. For tumor cell inoculation, 1×10⁶ M109 cells or 1×10⁶ KB cells in 100 μL are injected in the subcutis of the dorsal medial area. Tumors are measured in two perpendicular directions every 2-3 days using a caliper, and their volumes were calculated as $0.5 \times L \times W^2$, where L=measurement of longest axis in mm and W=measurement of axis perpendicular to L in mm. Log cell kill (LCK) and treated over control (T/C) values are then calculated according to published procedures (see, e.g., Lee et al., "BMS-247550: a novel epothilone analog with a mode of action similar to paclitaxel but possessing superior antitumor efficacy" Clin Cancer Res 7:1429-1437 (2001); Rose, "Taxol-based combination chemotherapy and other in vivo preclinical antitumor studies" J Natl Cancer Inst Monogr 47-53 (1993)). Dosing solutions are prepared fresh each day in PBS and administered through the lateral tail vein of the mice. Importantly, dosing is initiated when the s.c. tumors were between 50-100 mm³ in volume.

Persistent drug toxicity is assessed by collecting blood via cardiac puncture and submitting the serum for independent analysis of blood urea nitrogen (BUN), creatinine, total protein, AST-SGOT, ALT-SGPT plus a standard hematological cell panel at Ani-Lytics, Inc. (Gaithersburg, Md.). In addition, histopathologic evaluation of formalin-fixed heart, lungs, liver, spleen, kidney, intestine, skeletal muscle and bone (tibia/fibula) is conducted by board-certified pathologists at Animal Reference Pathology Laboratories (ARUP; Salt Lake City, Utah).

What is claimed is:

1. A process for converting a compound of the formula (I)

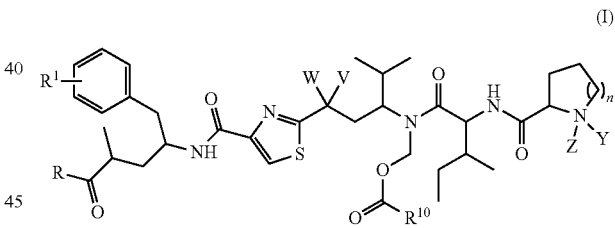

(I)

wherein:
  n is an integer from 1 to 3;
  V is selected from the group consisting of H, $OR^2$, and halo, and W is selected from the group consisting of H, $OR^2$, and alkyl; or V and W are taken together with the attached carbon to form a carbonyl;
  Z is alkyl, and Y is O; or Z is alkyl or $C(O)R^4$, and Y is absent;
  R is OH or a leaving group; or R forms a carboxylic acid derivative selected from the group consisting of an ester, an amide, an imide, and an acylhydrazide;
  $R^1$ is H; or $R^1$ represents 1 to 3 substituents each independently selected from the group consisting of halo, nitro, carboxylate, cyano, hydroxyl, alkyl, haloalkyl, alkoxy, haloalkoxy, and $OR^6$;
  each $R^2$ is independently selected from the group consisting of H, alkyl, and $C(O)R^5$, provided that $R^2$ is not H when both V and W are $OR^2$;
  $R^4$ is selected from the group consisting of alkyl, $CF_3$, and aryl;

each $R^5$ is independently selected from the group consisting of alkyl, cycloalkyl, alkenyl, arylalkyl and aryl;

$R^6$ is selected from the group consisting of aryl, $C(O)R^7$, $P(O)(OR^8)_2$, $SO_3R^8$, and a phenol protecting group;

each $R^7$ and $R^8$ is independently selected from the group consisting of H, alkyl, alkenyl, cycloalkyl, heterocyclyl, aryl, and arylalkyl; or $R^8$ is a metal cation; and $R^{10}$ is alkyl or alkenyl, each of which is optionally substituted;

into a compound of the formula (II)

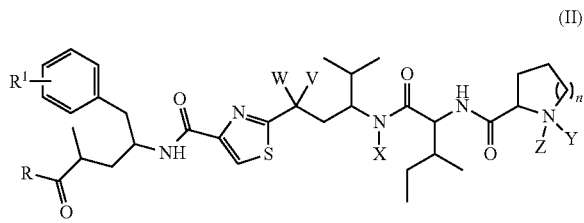

(II)

wherein:
n, V, W, Z, Y, R, $R^1$, $R^2$, $R^4$, $R^5$, $R^6$, $R^7$, $R^8$, and $R^{10}$ are as defined in formula I;

X is $CH_2QR^9$;

Q is —NH— or —S—, and each $R^9$ is independently selected from the group consisting of hydrogen, $C_{1-4}$ alkyl, alkenyl, aryl, and $C(O)R^{11}$; or Q is —O—, and $R^9$ is $C(O)R^{11}$ or $C_5$ alkyl; and each $R^{11}$ is independently selected from the group consisting of $C_{1-6}$ alkyl, alkenyl, aryl, and heteroaryl;

the process comprising (a) mixing the compound of the formula (I) with an acid to form an intermediate; and (b) reacting the intermediate with a nucleophile.

2. The process of claim 1, wherein the nucleophile is selected from the group consisting of 3-methylbutanol, 1-propanethiol, 2-sulfanylethanol, 1,2-ethanedithiol, acetic acid, butyric acid, trans-4-chloro-2-butenoic acid, and isovaleronitrile.

3. The process of claim 1, wherein the acid is trifluoroacetic acid.

4. A process for converting a compound of the formula (I)

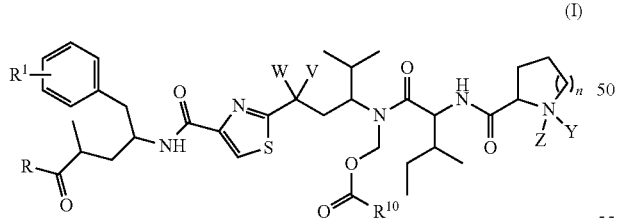

(I)

wherein:
n is an integer from 1 to 3;

V is selected from the group consisting of H, $OR^2$, and halo, and W is selected from the group consisting of H, $OR^2$, and alkyl; or V and W are taken together with the attached carbon to form a carbonyl;

Z is alkyl, and Y is O; or Z is alkyl or $C(O)R^4$, and Y is absent;

R is OH or a leaving group; or R forms a carboxylic acid derivative selected from the group consisting of an ester, an amide, an imide, and an acylhydrazide;

$R^1$ is H; or $R^1$ represents 1 to 3 substituents each independently selected from the group consisting of halo, nitro, carboxylate, cyano, hydroxyl, alkyl, haloalkyl, alkoxy, haloalkoxy, and $OR^6$;

each $R^2$ is independently selected from the group consisting of H, alkyl, and $C(O)R^5$, provided that $R^2$ is not H when both V and W are $OR^2$;

$R^4$ is selected from the group consisting of alkyl, $CF_3$, and aryl;

each $R^5$ is independently selected from the group consisting of alkyl, cycloalkyl, alkenyl, arylalkyl and aryl;

$R^6$ is selected from the group consisting of aryl, $C(O)R^7$, $P(O)(OR^8)_2$, $SO_3R^8$, and a phenol protecting group;

each $R^7$ and $R^8$ is independently selected from the group consisting of H, alkyl, alkenyl, cycloalkyl, heterocyclyl, aryl, and arylalkyl; or $R^8$ is a metal cation; and $R^{10}$ is alkyl or alkenyl;

into a compound of the formula (II)

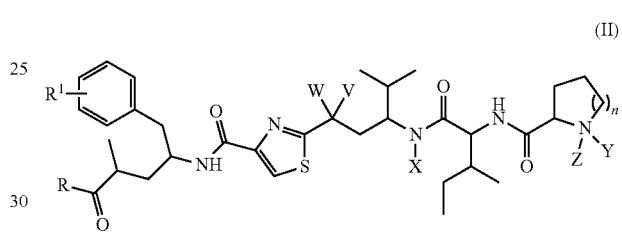

(II)

wherein:
n, V, W, Z, Y, R, $R^1$, $R^2$, $R^4$, $R^5$, $R^6$, $R^7$, $R^8$, and $R^{10}$ are as defined in formula I;

X is selected from the group consisting of $C_{1-4}$ alkyl, alkenyl, and $CH_2QR^9$;

Q is selected from the group consisting of —NH—, —O—, and —S—;

each $R^9$ is independently selected from the group consisting of hydrogen, $C_{1-5}$ alkyl, alkenyl, aryl, and $C(O)R^{11}$; and each $R^{11}$ is independently selected from the group consisting of $C_{1-6}$ alkyl, alkenyl, aryl, and heteroaryl;

the process comprising (a) mixing the compound of the formula (I) with trifluoroacetic acid to form an intermediate and (b) reacting the intermediate with a nucleophile.

5. The process of claim 4, wherein the nucleophile is a compound of the formula $R^{11}CO_2H$ or an anion thereof, wherein $R^{11}$ is as defined in formula II; or the nucleophile is a compound of the formula $R^9OH$ or an anion thereof, wherein $R^9$ is as defined in formula II; or the nucleophile is a compound of the formula $R^{21}CN$, wherein $R^{21}$ is selected from the group consisting of alkyl, alkenyl, cycloalkyl, aryl, and arylalkyl.

6. The process of claim 4, wherein the nucleophile is selected from the group consisting of methanol, 1-propanol, ethylene glycol, 3-methylbutanol, 1-propanethiol, 2-sulfanylethanol, 1,2-ethanedithiol, acetic acid, butyric acid, trans-4-chloro-2-butenoic acid, isovaleronitrile, and allyltrimethylsilane.

7. The process of claim 4, wherein the second compound is tubulysin B and the nucleophile is butyric acid.

8. A process for converting a compound of the formula (I)

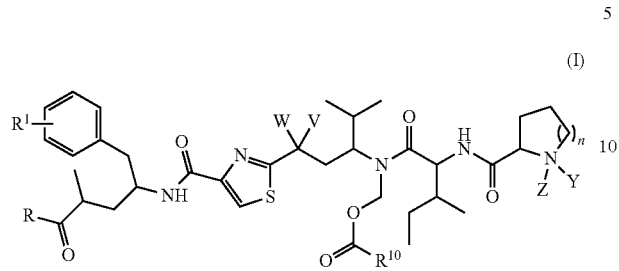

wherein:

n is an integer from 1 to 3;

V is selected from the group consisting of H, $OR^2$, and halo, and W is selected from the group consisting of H, $OR^2$, and alkyl; or V and W are taken together with the attached carbon to form a carbonyl;

Z is alkyl, and Y is O; or Z is alkyl or $C(O)R^4$, and Y is absent;

R is OH or a leaving group; or R forms a carboxylic acid derivative selected from the group consisting of an ester, an amide, an imide, and an acylhydrazide;

$R^1$ is H; or $R^1$ represents 1 to 3 substituents each independently selected from the group consisting of halo, nitro, carboxylate, cyano, hydroxyl, alkyl, haloalkyl, alkoxy, haloalkoxy, and $OR^6$;

each $R^2$ is independently selected from the group consisting of H, alkyl, and $C(O)R^5$, provided that $R^2$ is not H when both V and W are $OR^2$;

$R^4$ is selected from the group consisting of alkyl, $CF_3$, and aryl;

each $R^5$ is independently selected from the group consisting of alkyl, cycloalkyl, alkenyl, arylalkyl and aryl;

$R^6$ is selected from the group consisting of aryl, $C(O)R^7$, $P(O)(OR^8)_2$, $SO_3R^8$, and a phenol protecting group;

each $R^7$ and $R^8$ is independently selected from the group consisting of H, alkyl, alkenyl, cycloalkyl, heterocyclyl, aryl, and arylalkyl; or $R^8$ is a metal cation;

and $R^{10}$ is alkyl or alkenyl;

into a compound of the formula (II)

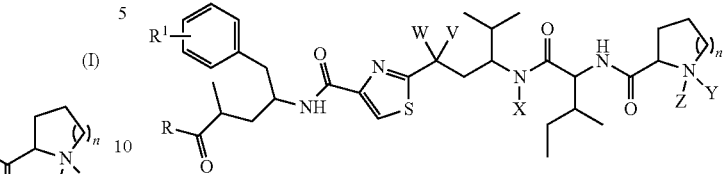

wherein:

n, V, W, Z, Y, R, $R^1$, $R^2$, $R^4$, $R^5$, $R^6$, $R^7$, $R^8$, and $R^{10}$ are as defined in formula I;

X is $CH_2OR^9$;

each $R^9$ is independently selected from the group consisting of $C_{1-5}$ alkyl, alkenyl, aryl, and $C(O)R^{11}$; and each $R^{11}$ is independently selected from the group consisting of $C_{1-6}$ alkyl, alkenyl, aryl, or heteroaryl;

the process comprising (a) mixing the compound of the formula (I) with trifluoroacetic acid to form an intermediate; and (b) reacting the intermediate with a nucleophile.

9. The process of claim 8, wherein the nucleophile is a compound of the formula $R^{11}CO_2H$ or an anion thereof, wherein $R^{11}$ is as defined in formula II; or the nucleophile is a compound of the formula $R^9OH$ or an anion thereof, wherein $R^9$ is as defined in formula II.

10. The process of claim 8, wherein the nucleophile is selected from the group consisting of methanol, 1-propanol, ethylene glycol, 3-methylbutanol, acetic acid, and butyric acid.

11. The process of claim 8, wherein $R^9$ is $C_{1-5}$ alkyl.

12. The process of claim 8, wherein $R^9$ is $C(O)R^{11}$, and $R^{11}$ is $C_{1-6}$ alkyl.

13. The process of claim 8, wherein $R^9$ is $C(O)R^{11}$, $R^{11}$ is $-CH_2CH_2CH_3$, and the nucleophile is butyric acid.

14. The process of claim 8, wherein the first compound is mixed with trifluoroacetic acid under substantially anhydrous conditions.

15. The process of claim 8, wherein R is OH or forms an acylhydrazide.

16. The process of claim 8, wherein n is 2.

17. The process of claim 8, wherein V is H, W is $OR^2$, $R^2$ is $C(O)R^5$, and $R^5$ is alkyl.

18. The process of claim 8, wherein Z is alkyl, and Y is absent.

19. The process of claim 10, wherein $R^1$ represents 1 substituent that is OH, or $R^1$ is H.

20. The process of claim 10, wherein the compound of the formula I is of the formula (III)

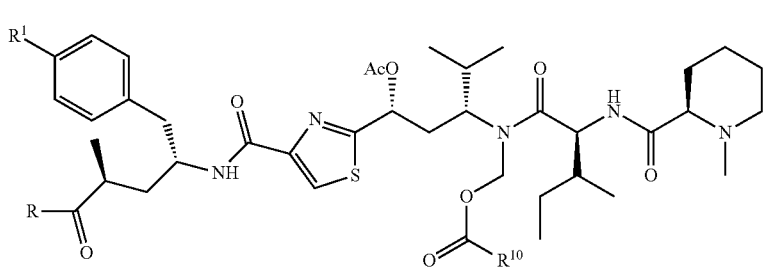

wherein:

R, $R^1$, $R^6$, $R^7$, $R^8$, and $R^{10}$ are as defined in formula I.

* * * * *